US012599362B2

(12) United States Patent
Sakamoto et al.

(10) Patent No.: US 12,599,362 B2
(45) Date of Patent: Apr. 14, 2026

(54) IMAGE PROCESSING DEVICE, IMAGE PROCESSING SYSTEM, IMAGE DISPLAY METHOD, AND IMAGE PROCESSING PROGRAM

(71) Applicant: TERUMO KABUSHIKI KAISHA, Tokyo (JP)

(72) Inventors: Yasukazu Sakamoto, Hiratsuka (JP); Katsuhiko Shimizu, Fujinomiya (JP); Hiroyuki Ishihara, Tokyo (JP); Clément Jacquet, Sakai (JP); Stephen Tchen, Sakai (JP); Thomas Henn, Sakai (JP); Ryosuke Saga, Sakai (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 180 days.

(21) Appl. No.: 18/304,692

(22) Filed: Apr. 21, 2023

(65) Prior Publication Data

US 2023/0255569 A1     Aug. 17, 2023

Related U.S. Application Data

(63) Continuation of application No. PCT/JP2021/035459, filed on Sep. 27, 2021.

(30) Foreign Application Priority Data

Oct. 22, 2020     (JP) ................................ 2020-177636

(51) Int. Cl.
*A61B 8/00* (2006.01)
*A61B 5/00* (2006.01)
(Continued)

(52) U.S. Cl.
CPC .............. *A61B 8/12* (2013.01); *A61B 5/0066* (2013.01); *A61B 5/0084* (2013.01); *A61B 8/0891* (2013.01); *A61B 8/463* (2013.01)

(58) Field of Classification Search
CPC ......... G06T 19/00–20; G06T 2219/008; G06T 2219/016; G06T 2219/028;
(Continued)

(56) References Cited

U.S. PATENT DOCUMENTS 6,251,072 B1     6/2001   Ladak et al.
6,385,332 B1     5/2002   Zahalka et al.
(Continued)

FOREIGN PATENT DOCUMENTS

JP          2004344185 A     12/2004
JP          2005118160 A      5/2005
(Continued)

OTHER PUBLICATIONS

Definition of "Indicate", retrieved May 7, 2025.*
(Continued)

*Primary Examiner* — Carolyn A Pehlke
(74) *Attorney, Agent, or Firm* — Buchanan Ingersoll & Rooney PC

(57) ABSTRACT

An image processing device is an image processing device that causes a display to display, as a three-dimensional image, three-dimensional data representing a biological tissue. The image processing device includes: a control unit configured to form, in the three-dimensional data, a cutting region for exposing a lumen of the biological tissue in the three-dimensional image, and to display, on the display, a two-dimensional image representing a portion corresponding to the cutting region in one cross section of the biological tissue at a position corresponding to the one cross section in the three-dimensional image.

9 Claims, 19 Drawing Sheets

(51) Int. Cl.
    *A61B 8/08*        (2006.01)
    *A61B 8/12*        (2006.01)

(58) Field of Classification Search
    CPC ............. G06T 2219/2016; G06T 15/10; A61B
                         8/0891; A61B 8/12; A61B 8/463
    See application file for complete search history.

(56)                  References Cited

U.S. PATENT DOCUMENTS

| 2005/0090743 | A1 | | 4/2005 | Kawashima et al. | |
|---|---|---|---|---|---|
| 2006/0084872 | A1 | | 4/2006 | Ichikawa et al. | |
| 2008/0228086 | A1 | | 9/2008 | Ilegbusi et al. | |
| 2010/0215238 | A1 | | 8/2010 | Lu et al. | |
| 2014/0039294 | A1 | | 2/2014 | Jiang | |
| 2017/0024532 | A1 | * | 1/2017 | Gopinath | ............. A61B 5/6876 |
| 2019/0005612 | A1 | * | 1/2019 | Aguirre-Valencia | ... G06T 19/20 |
| 2021/0015452 | A1 | * | 1/2021 | Shimizu | ............... A61B 5/0073 |

FOREIGN PATENT DOCUMENTS

| JP | 2005160616 | A | | 6/2005 | |
|---|---|---|---|---|---|
| WO | WO-2019189518 | A1 | * | 10/2019 | ........... A61B 5/0073 |

OTHER PUBLICATIONS

International Search Report (PCT/ISA/210) with translation and Written Opinion (PCT/ISA/237) mailed on Nov. 9, 2021, by the Japan Patent Office as the International Searching Authority for International Application No. PCT/JP2021/035459. (8 pages).

\* cited by examiner

IMAGE PROCESSING DEVICE, IMAGE PROCESSING SYSTEM, IMAGE DISPLAY METHOD, AND IMAGE PROCESSING PROGRAM

CROSS-REFERENCES TO RELATED APPLICATIONS

This application is a continuation of International Application No. PCT/JP2021/035459 filed on Sep. 27, 2021, which claims priority to Japanese Application No. 2020-177636 filed on Oct. 22, 2020, the entire content of both of which is incorporated herein by reference.

TECHNOLOGICAL FIELD

The present disclosure generally relates to an image processing device, an image processing system, an image display method, and an image processing program.

BACKGROUND DISCUSSION

U.S. Patent Application Publication No. 2010/0215238, U.S. Pat. Nos. 6,385,332, and 6,251,072 describe a technique for generating a three-dimensional image of a cardiac cavity or a blood vessel using an ultrasound (US) imaging system.

Treatment using intravascular ultrasound (IVUS) is widely performed for a cardiac cavity, a cardiac blood vessel, a lower limb artery region, and the like. IVUS is a device or a method that provides a two-dimensional image of a plane perpendicular to a longitudinal axis of a catheter.

At present, an operator needs to execute an operation while reconstructing a three-dimensional structure by laminating two-dimensional images of IVUS in his/her head, which can be a barrier particularly for young doctors or inexperienced doctors. In order to remove such a barrier, it is conceivable to automatically generate a three-dimensional image representing a structure of a biological tissue such as the cardiac cavity or the blood vessel from the two-dimensional images of IVUS and display the generated three-dimensional image to the operator.

However, in two-dimensional images of IVUS, the tissue surrounding the cardiac cavity or the blood vessel lumen is shown. In addition, by displaying the generated three-dimensional image as it is generated, the operator can see only an outer wall of the tissue and cannot see the inside of the biological tissue to execute or perform an operation. Therefore, it would be desirable to cut-out (i.e., remove from the image) a part of the structure of the biological tissue in the three-dimensional image so that the lumen can be seen. At this time, if the information of the cut-out region is not shown, it can be difficult to grasp where in the biological tissue the operator is seeing. Therefore, it is desirable to be able to supplement information of the cut-out region.

SUMMARY

The present disclosure provides supplemental information about a cut-out portion of the structure of a biological tissue.

An image processing device according to an aspect of the present disclosure is an image processing device that causes a display to display, as a three-dimensional image, three-dimensional data representing a biological tissue, the image processing device. The image processing device includes: a control unit that performs control of forming, in the three-dimensional data, a cutting region for exposing a lumen of the biological tissue in the three-dimensional image, and displaying a two-dimensional image representing a portion corresponding to the cutting region in one cross section of the biological tissue at a position corresponding to the one cross section in the three-dimensional image.

In one embodiment, the control unit performs control of generating and updating the three-dimensional data based on tomographic data acquired by a sensor that acquires tomographic data of the biological tissue while moving in a lumen of the biological tissue, and displaying, as the two-dimensional image, an image representing a portion corresponding to the cutting region in a cross section indicated by tomographic data newly acquired by the sensor at a position corresponding to a cross section indicated by the newly acquired tomographic data in the three-dimensional image every time new tomographic data is acquired by the sensor.

In one embodiment, the control unit sets a viewpoint when the three-dimensional image is displayed by positioning a virtual camera in a three-dimensional space, and in a case where the camera is not on a plane corresponding to the one cross section in the three-dimensional image, the control unit performs control of displaying the two-dimensional image on the plane.

In one embodiment, in a case where the camera is on the plane, the control unit performs control of displaying the two-dimensional image in inclination with respect to the plane.

In one embodiment, the control unit performs control of displaying the two-dimensional image on a window other than a window on which the three-dimensional image is displayed in a case where the camera is on the plane.

In one embodiment, the control unit sets a viewpoint when the three-dimensional image is displayed by positioning a virtual camera in a three-dimensional space, and adjusts an angle at which the two-dimensional image is displayed with respect to the plane regardless of whether the camera is on a plane corresponding to the one cross section in the three-dimensional image to maintain an angle formed between a line of sight from the camera to the two-dimensional image and the two-dimensional image at a fixed angle.

In one embodiment, the control unit sets a viewpoint when the three-dimensional image is displayed by positioning a virtual camera in a three-dimensional space, and adjusts an angle at which the two-dimensional image is displayed with respect to the plane regardless of whether the camera is on a plane corresponding to the one cross section in the three-dimensional image to maintain an absolute value of the angle at a fixed value.

In one embodiment, the control unit performs control of displaying the two-dimensional image in inclination obliquely downward with respect to the plane in a case where the camera is above the plane, and displaying the two-dimensional image in inclination obliquely upward with respect to the plane in a case where the camera is below the plane.

An image processing system according to an aspect of the present disclosure includes the image processing device; and a probe including a sensor that acquires tomographic data of the biological tissue while moving in a lumen of the biological tissue.

In one embodiment, the image processing system further includes the display.

An image display method according to an aspect of the present disclosure is an image display method for causing a display to display, as a three-dimensional image, three-dimensional data representing a biological tissue, the image display method comprising: forming, by a computer, in the three-dimensional data, a cutting region for exposing a lumen of the biological tissue in the three-dimensional image; and controlling, by the computer, of displaying a two-dimensional image representing a portion corresponding to the cutting region in one cross section of the biological tissue at a position corresponding to the one cross section in the three-dimensional image.

A non-transitory computer-readable medium (CRM) storing computer program code, according to an aspect of the present disclosure, executed by a computer processor that causes a display to display, as a three-dimensional image, three-dimensional data representing a biological tissue, and that executes an imaging process including: forming, in the three-dimensional data, a cutting region for exposing a lumen of the biological tissue in the three-dimensional image; and controlling of displaying a two-dimensional image representing a portion corresponding to the cutting region in one cross section of the biological tissue at a position corresponding to the one cross section in the three-dimensional image.

According to the present disclosure, it is possible to supplement information about a cut-out portion of the structure of a biological tissue.

DETAILED DESCRIPTION

Figure 1:
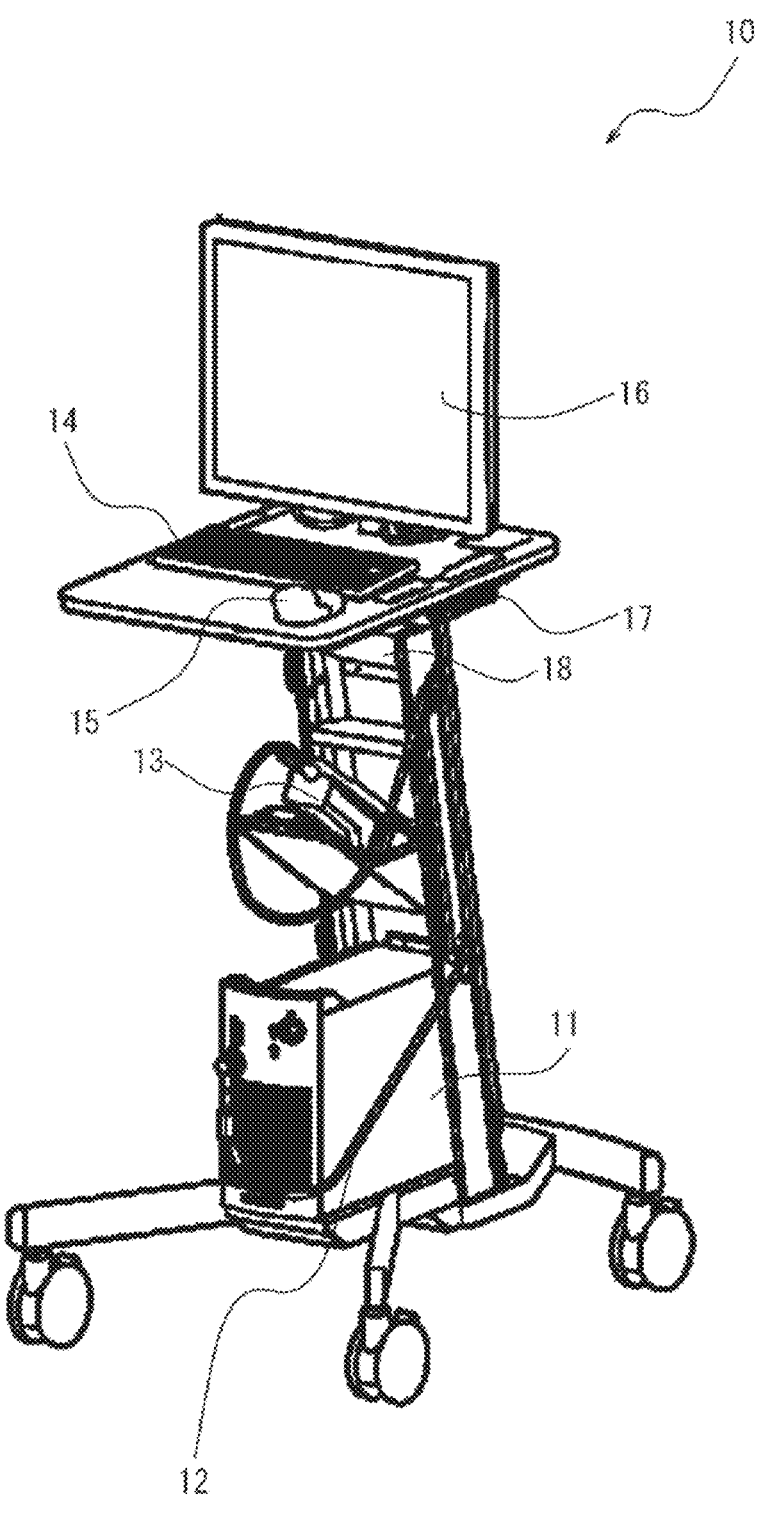
FIG. 1 is a perspective view of an image processing system according to an embodiment of the present disclosure.

Set forth below with reference to the accompanying drawings is a detailed description of embodiments of an image processing device, an image processing system, an image display method, and an image processing program.

In the drawings, the same or corresponding parts are denoted by the same reference numerals. In the description of the present embodiment, the description of the same or corresponding parts will be omitted or simplified as appropriate.

An outline of the present embodiment will be described with reference to FIGS. 1-4, and 6.

Figure 2:
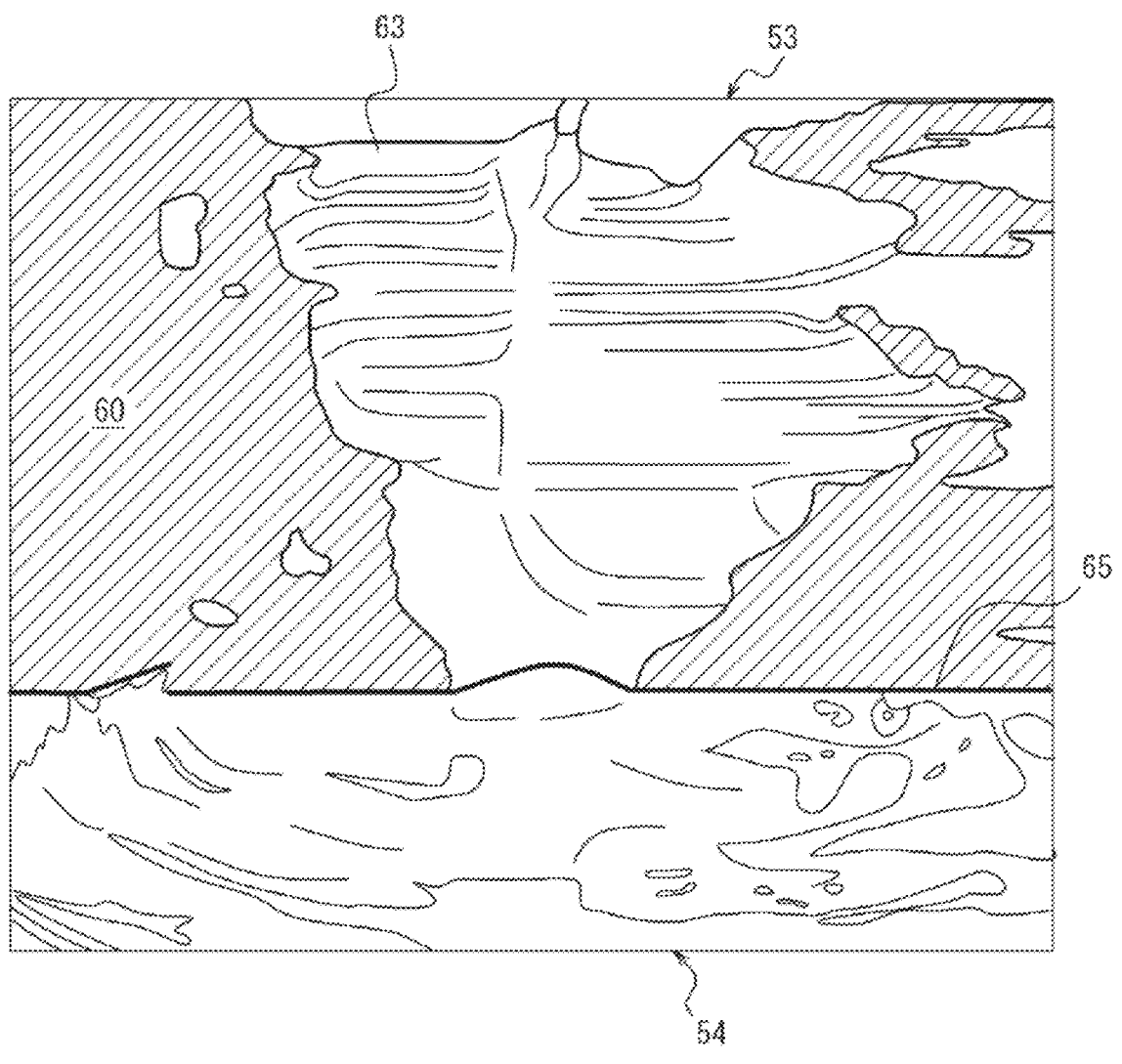
FIG. 2 is a diagram illustrating an example of an image displayed on a display by the image processing system according to the embodiment of the present disclosure.
Figure 4:
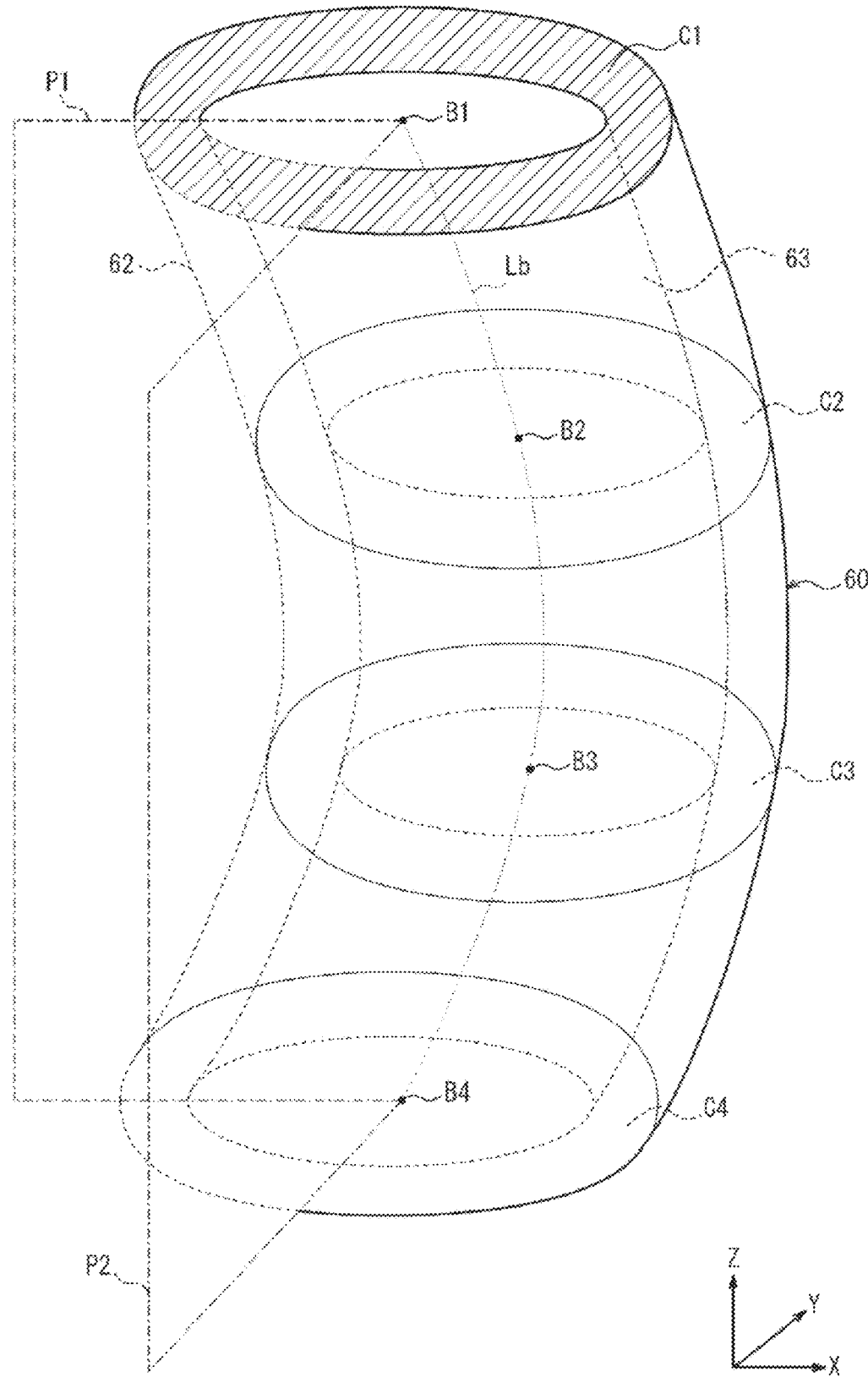
FIG. 4 is a diagram illustrating an example of a cutting region formed by the image processing system according to the embodiment of the present disclosure.

An image processing device 11 according to the present embodiment is a computer that causes a display 16 to display, as a three-dimensional image 53, three-dimensional data 52 representing a biological tissue 60. As illustrated in FIG. 4, the image processing device 11 forms, in the three-dimensional data 52, a cutting region 62 for exposing a lumen 63 of the biological tissue 60 in the three-dimensional image 53. The image processing device 11 performs control of displaying a two-dimensional image 54 representing a portion corresponding to the cutting region 62 in one cross section Ci of the biological tissue 60 at a position 65 corresponding to the one cross section Ci in the three-dimensional image 53 as illustrated in FIG. 2.

According to the present embodiment, a part of the structure of the biological tissue 60 is cut out in the three-dimensional image 53, so that the lumen 63 of the biological tissue 60 can be seen. At this time, it can be difficult to grasp where in the entire biological tissue 60 an operator is seeing if the information of the cut-out region (or cut-out area) is missing. However, in the present embodiment, it is possible to supplement the information of the region by displaying the two-dimensional image 54 representing the portion corresponding to the region.

In the present embodiment, the image processing device 11 generates and updates the three-dimensional data 52 based on tomographic data 51 acquired by a sensor that acquires the tomographic data 51 while moving in the lumen 63 of the biological tissue 60. Every time new tomographic data 51 is acquired by the sensor, the image processing device 11 performs control of displaying an image representing the portion corresponding to the cutting region 62 in the cross section indicated by the tomographic data 51 newly acquired by the sensor, as the two-dimensional image 54, at the position 65 corresponding to the cross-section indicated by the newly acquired tomographic data 51 in the three-dimensional image 53. That is, in the present embodiment, the cross section Ci is a cross section indicated by the tomographic data 51 acquired last by the sensor.

According to the present embodiment, the cross section of the biological tissue 60 indicated by the tomographic data 51 newly acquired by the sensor can be displayed at a position where the sensor currently exists. Therefore, the missing information can be substituted by the information currently obtained by the sensor, that is, the latest information.

In the present embodiment, an image corresponding to the current position of the sensor, that is, the latest image is always displayed as the two-dimensional image 54, but as a modification of the present embodiment, an image corresponding to a position other than the current position of the sensor may be displayed as the two-dimensional image 54.

Figure 3:
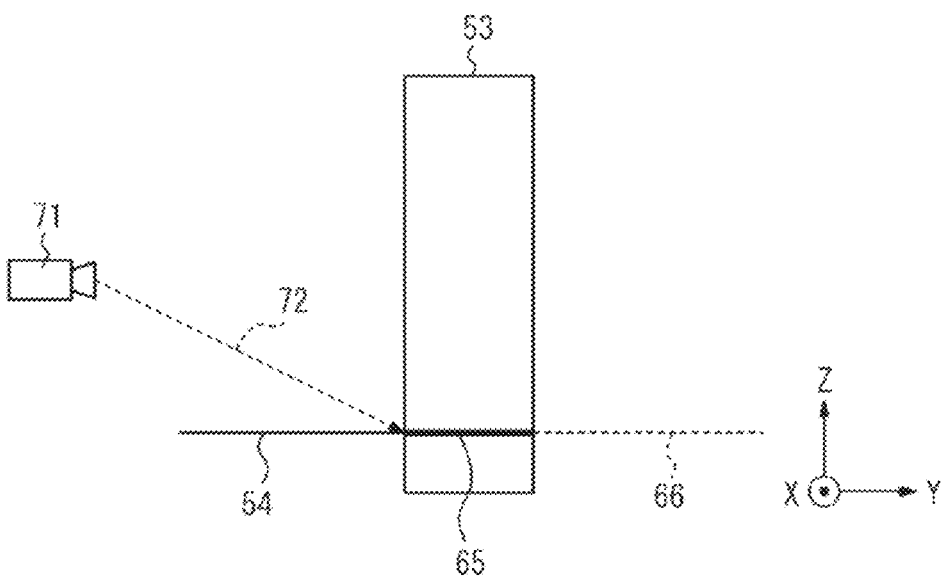
FIG. 3 is a diagram illustrating an example of a positional relationship between an image set by the image processing system according to the embodiment of the present disclosure and a camera.

In the present embodiment, the image processing device 11 sets a viewpoint when the three-dimensional image 53 is displayed by positioning a virtual camera 71 in the three-dimensional space. As illustrated in FIG. 3, in a case where the camera 71 is not on a plane 66 corresponding to the cross section Ci in the three-dimensional image 53, the image processing device 11 performs control of displaying the two-dimensional image 54 on the plane 66.

The biological tissue 60 includes, for example, an organ such as a blood vessel or a heart. The biological tissue 60 is not limited to only an anatomically single organ or a part of the organ, but also includes a tissue having a lumen across a plurality of organs. An example of such a tissue is, specifically, a part of the vascular tissue extending from the upper part of the inferior vena cava to the lower part of the superior vena cava through the right atrium. In the examples of FIGS. 2 and 4, the biological tissue 60 is a blood vessel.

In FIGS. 3 and 4, the X direction and the Y direction orthogonal to the X direction correspond to the lateral directions of the lumen 63 of the biological tissue 60. The Z direction orthogonal to the X direction and the Y direction corresponds to the longitudinal direction of the lumen 63 of the biological tissue 60.

In the example of FIG. 4, the image processing device 11 calculates the positions of centroids B1, B2, B3, and B4 of cross sections C1, C2, C3, and C4 of the biological tissue 60 using the three-dimensional data 52. The image processing device 11 sets two planes intersecting at a single line Lb passing through the positions of the centroids B1, B2, B3, and B4 as cutting planes P1 and P2. The image processing device 11 forms, in the three-dimensional data 52, a region interposed between the cutting planes P1 and P2 in the three-dimensional image 53 and from which the lumen 63 of the biological tissue 60 is exposed, as the cutting region 62.

In the case of the three-dimensional model of the bent blood vessel as illustrated in FIG. 4, there is a case where the inside of the blood vessel cannot be correctly displayed if the three-dimensional model is cut at one plane to display the lumen 63. In the present embodiment, as illustrated in FIG. 4, by continuously capturing the centroids of the blood vessel, the three-dimensional model can be cut such that the inside of the blood vessel can be reliably displayed.

In FIG. 4, for convenience, four cross sections C1, C2, C3, and C4 are illustrated as a plurality of lateral cross sections of the lumen 63 of the biological tissue 60, but the number of cross sections serving as calculation targets of the centroid positions is not limited to four, and is preferably the same as the number of cross-sectional images acquired by IVUS.

As an example different from FIG. 4, the centroid is not necessarily used. In such an example, the image processing device 11 sets two planes intersecting at any one line, such as a straight line extending in the Z direction, as the cutting planes P1 and P2.

A configuration of an image processing system 10 according to the present embodiment will be described with reference to FIG. 1.

The image processing system 10 can include the image processing device 11, a cable 12, a drive unit 13, a keyboard 14, a mouse 15, and the display 16.

In the present embodiment, the image processing device 11 is a dedicated computer specialized for image diagnosis, but may be a general-purpose computer such as a personal computer (PC).

The cable 12 is used to connect the image processing device 11 and the drive unit 13.

Figure 5:
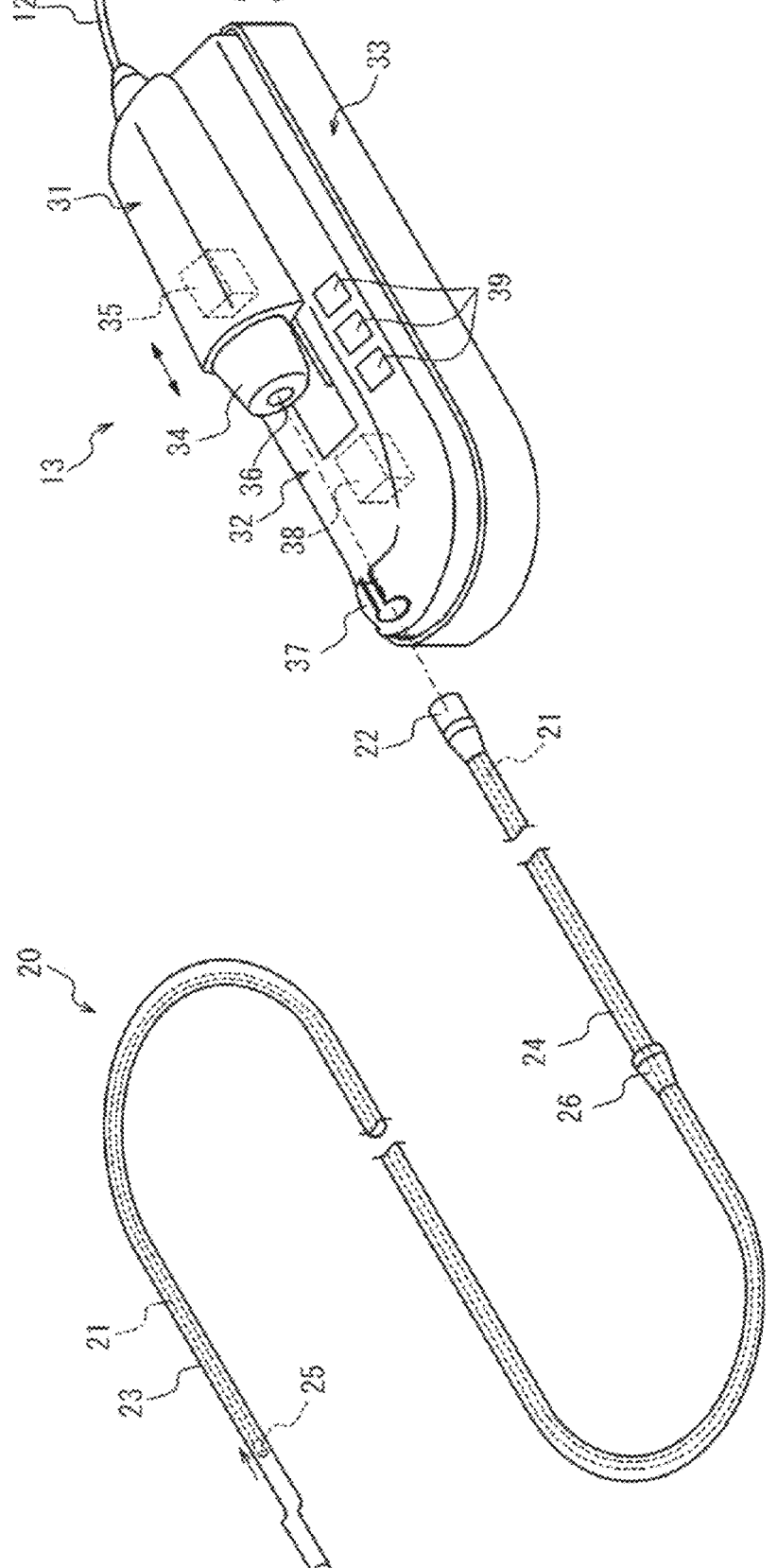
FIG. 5 is a perspective view of a probe and a drive unit according to the embodiment of the present disclosure.

The drive unit 13 is a device that is used by being connected to a probe 20 illustrated in FIG. 5 and drives the probe 20. The drive unit 13 is also referred to as a motor drive unit (MDU). The probe 20 is applied to IVUS. The probe 20 is also called an IVUS catheter or an image diagnosis catheter.

The keyboard 14, the mouse 15, and the display 16 are connected to the image processing device 11 via a cable or wirelessly. The display 16 can be, for example, a liquid crystal display (LCD), an organic electro luminescence (EL) display, or a head-mounted display (HMD).

The image processing system 10 optionally further includes a connection terminal 17 and a cart unit 18.

The connection terminal 17 is used to connect the image processing device 11 and an external device. The connection terminal 17 can be, for example, a universal serial bus (USB) terminal. The external device can be, for example, a recording medium such as a magnetic disk drive, a magneto-optical disk drive, or an optical disk drive.

The cart unit 18 can be a cart with a caster for movement. The image processing device 11, the cable 12, and the drive unit 13 can be installed in the cart body of the cart unit 18. The keyboard 14, the mouse 15, and the display 16 can be installed on the uppermost table of the cart unit 18.

Configurations of the probe 20 and the drive unit 13 according to the present embodiment will be described with reference to FIG. 5.

The probe 20 can include a drive shaft 21, a hub 22, a sheath 23, an outer tube 24, an ultrasound transducer 25, and a relay connector 26.

The drive shaft 21 passes through the sheath 23 inserted into the body cavity of the living body and the outer tube 24 connected to the proximal end of the sheath 23, and extends to the inside of the hub 22 disposed at the proximal end of the probe 20. The drive shaft 21 is rotatably disposed in the sheath 23 and the outer tube 24 with an ultrasound transducer 25 that transmits and receives a signal at the distal end. The relay connector 26 connects the sheath 23 and the outer tube 24.

The hub 22, the drive shaft 21, and the ultrasound transducer 25 are connected to each other to integrally move forward and backward in the axial direction. Therefore, for example, when the hub 22 is pushed toward the distal end, the drive shaft 21 and the ultrasound transducer 25 move toward the distal end inside the sheath 23. For example, when the hub 22 is pulled toward the proximal end, the drive shaft 21 and the ultrasound transducer 25 move toward the proximal end inside the sheath 23 as indicated by arrows.

The drive unit 13 can include a scanner unit 31, a slide unit 32, and a bottom cover 33.

The scanner unit 31 is connected to the image processing device 11 via the cable 12. The scanner unit 31 can include a probe connection portion 34 connected to the probe 20 and a scanner motor 35 as a drive source for rotating the drive shaft 21.

The probe connection portion 34 is detachably connected to the probe 20 via an insertion port 36 of the hub 22 disposed at the proximal end of the probe 20. In the hub 22, the proximal end of the drive shaft 21 is rotatably supported, and the rotational force of the scanner motor 35 is transmitted to the drive shaft 21. In addition, signals are transmitted and received between the drive shaft 21 and the image processing device 11 via the cable 12. In the image processing device 11, generation of a tomographic image of a biological lumen and image processing are performed based on a signal transmitted from the drive shaft 21.

The slide unit 32 is mounted with the scanner unit 31 to be movable forward and backward, and is mechanically and electrically connected to the scanner unit 31. The slide unit 32 can include a probe clamp portion 37, a slide motor 38, and a switch group 39.

The probe clamp portion 37 is disposed coaxially with the probe connection portion 34 at a position distal of the probe connection portion 34, and supports the probe 20 connected to the probe connection portion 34.

The slide motor 38 is a drive source that generates a drive force in the axial direction. The scanner unit 31 moves forward and backward by the drive of the slide motor 38, and the drive shaft 21 moves forward and backward in the axial direction accordingly. The slide motor 38 can be, for example, a servo motor.

The switch group 39 can include, for example, a forward switch and a pull-back switch that are pressed at the time of the forward and backward operation of the scanner unit 31, and a scan switch that is pressed at the time of the start and end of image depiction. The present disclosure is not limited to the examples described herein, and various switches are included in the switch group 39 as necessary.

When the forward switch is pressed, the slide motor 38 rotates forward, and the scanner unit 31 moves forward. On the other hand, when the pull-back switch is pressed, the slide motor 38 reversely rotates, and the scanner unit 31 moves backward.

When the scan switch is pressed, image depiction is started, the scanner motor 35 is driven, and the slide motor 38 is driven to move the scanner unit 31 backward. A user such as an operator connects the probe 20 to the scanner unit 31 in advance, and causes the drive shaft 21 to move toward the proximal end in the axial direction while rotating at the start of image depiction. When the scan switch is pressed again, the scanner motor 35 and the slide motor 38 are stopped, and image depiction ends.

The bottom cover 33 covers the entire periphery of the bottom surface and the side surface on the bottom surface side of the slide unit 32, and can approach and separate from the bottom surface of the slide unit 32.

Figure 6:
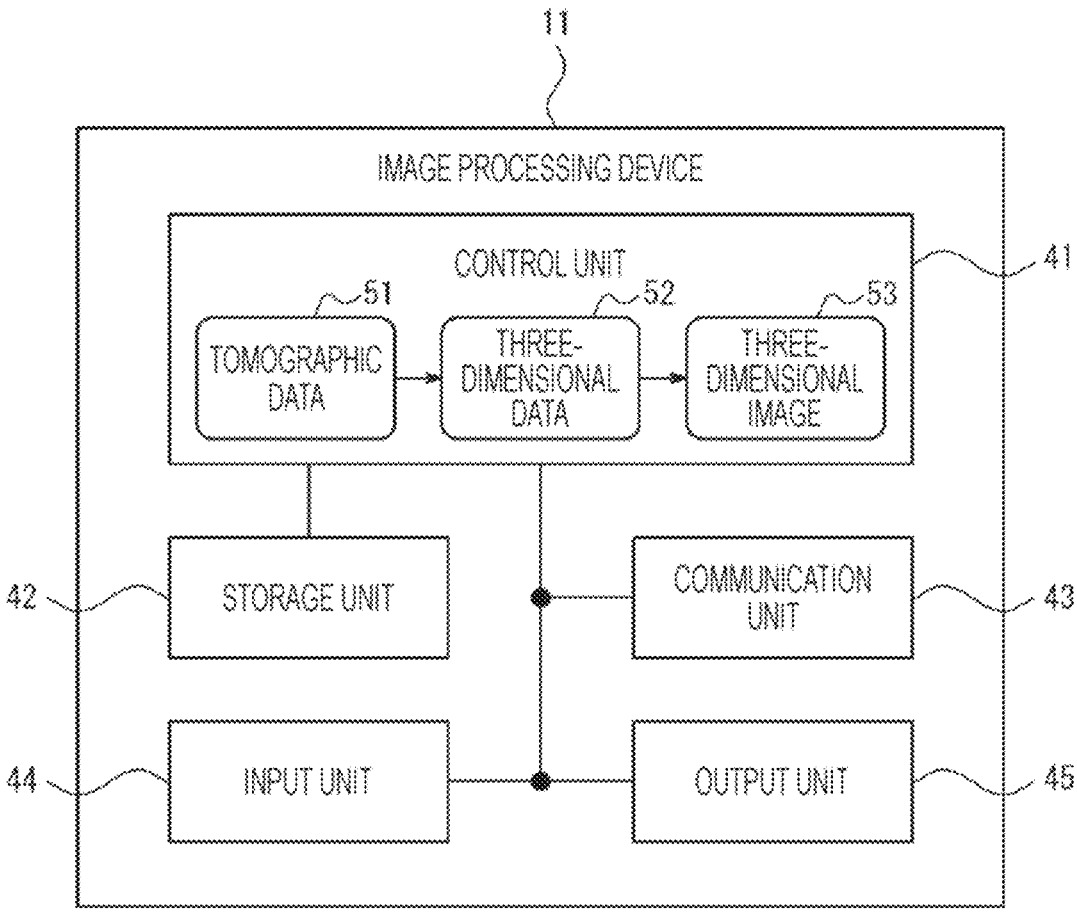
FIG. 6 is a block diagram illustrating a configuration of an image processing device according to the embodiment of the present disclosure.

A configuration of the image processing device 11 will be described with reference to FIG. 6.

The image processing device 11 can include a control unit 41, a storage unit 42, a communication unit 43, an input unit 44, and an output unit 45.

The control unit 41 can include at least one processor, at least one programmable circuit, at least one dedicated circuit, or any combination of the at least one processor, the at least one programmable circuit, and the at least one dedicated circuit. The processor can be, for example, a general-purpose processor such as a central processing unit (CPU) or a graphics processing unit (GPU), or a dedicated processor specialized for specific processing. The programmable circuit can be, for example, a field-programmable gate array (FPGA). The dedicated circuit can be, for example, an application specific integrated circuit (ASIC). The control unit 41 executes processing related to the operation of the image processing device 11 while controlling each unit of the image processing system 10 including the image processing device 11.

The storage unit 42 can include at least one semiconductor memory, at least one magnetic memory, at least one optical memory, or any combination of the at least one semiconductor memory, the at least one magnetic memory, and the at least one optical memory. The semiconductor memory can be, for example, a random access memory (RAM) or a read only memory (ROM). The RAM can be, for example, a static random access memory (SRAM) or a dynamic random access memory (DRAM). The ROM can be, for example, an electrically erasable programmable read only memory (EEPROM). The storage unit 42 can function as, for example, a main storage device, an auxiliary storage device, or a cache memory. The storage unit 42 stores data to be used for the operation of the image processing device 11 such as the tomographic data 51 and data obtained by the operation of the image processing device 11 such as the three-dimensional data 52 and the three-dimensional image 53.

The communication unit 43 includes at least one communication interface. The communication interface can be, for example, a wired local area network (LAN) interface, a wireless LAN interface, or an image diagnosis interface that receives and analog to digital (ND) converts an IVUS signal. The communication unit 43 receives data to be used for the operation of the image processing device 11 and transmits data obtained by the operation of the image processing device 11. In the present embodiment, the drive unit 13 is connected to the image diagnosis interface included in the communication unit 43.

The input unit 44 includes at least one input interface. The input interface can be, for example, a USB interface, a High-Definition Multimedia Interface (HDMI®) interface, or an interface compatible with near-field communication standard, such as Bluetooth®. The input unit 44 receives a user's operation such as an operation of inputting data to be used for the operation of the image processing device 11. In the present embodiment, the keyboard 14 and the mouse 15 are connected to a USB interface or an interface compatible with near-field communication included in the input unit 44. In a case where the touch screen is disposed integrally with the display 16, the display 16 may be connected to the USB interface or the HDMI interface included in the input unit 44.

The output unit 45 includes at least one output interface. The output interface can be, for example, a USB interface, an HDMI interface, or an interface compatible with near-field communication standard, such as Bluetooth. The output unit 45 outputs data obtained by the operation of the image processing device 11. In the present embodiment, the display 16 is connected to a USB interface or an HDMI interface included in the output unit 45.

A function of the image processing device 11 is implemented by executing an image processing program according to the present embodiment by a processor serving as the control unit 41. That is, the function of the image processing device 11 is implemented by software. The image processing program causes a computer to execute the operation of the image processing device 11 to cause the computer to function as the image processing device 11. That is, the computer functions as the image processing device 11 by executing the operation of the image processing device 11 according to the image processing program.

The program can be stored in a non-transitory computer-readable medium. The non-transitory computer-readable medium can be, for example, a flash memory, a magnetic recording device, an optical disc, a magneto-optical recording medium, or a ROM. The distribution of the programs can be performed, for example, by selling, transferring, or lending a portable medium, such as a Secure Digital (SD) card, a digital versatile disc (DVD), or a compact disc read only memory (CD-ROM), storing the programs. The programs may be distributed by storing the programs in a storage of a server and transferring the programs from the server to another computer. The program may be provided as a program product.

The computer temporarily stores, for example, the program stored in the portable medium or the program transferred from the server in a main storage device. Then, the computer reads the program stored in the main storage device by the processor, and executes processing according to the read program by the processor. The computer may read the program directly from the portable medium and execute the processing according to the program. Each time the program is transferred from a server to a computer, the computer may sequentially execute processing according to the received program. The programs may not be transferred from a server to a computer, but the processing may be executed by what is called an application service provider (ASP) service in which the functions are implemented only by execution instructions and result acquisition. The programs include information that is used for processing by a computer and is equivalent to the programs. For example, data that is not a direct command to the computer but has a property that defines processing of the computer corresponds to the "information equivalent to the program".

Some or all of the functions of the image processing device 11 may be implemented by a programmable circuit or a dedicated circuit as the control unit 41. That is, some or all of the functions of the image processing device 11 may be implemented by hardware.

An operation of the image processing system 10 according to the present embodiment will be described with reference to FIGS. 7 and 8. The operation of the image processing system 10 corresponds to an image display method according to the present embodiment.

Figure 7:
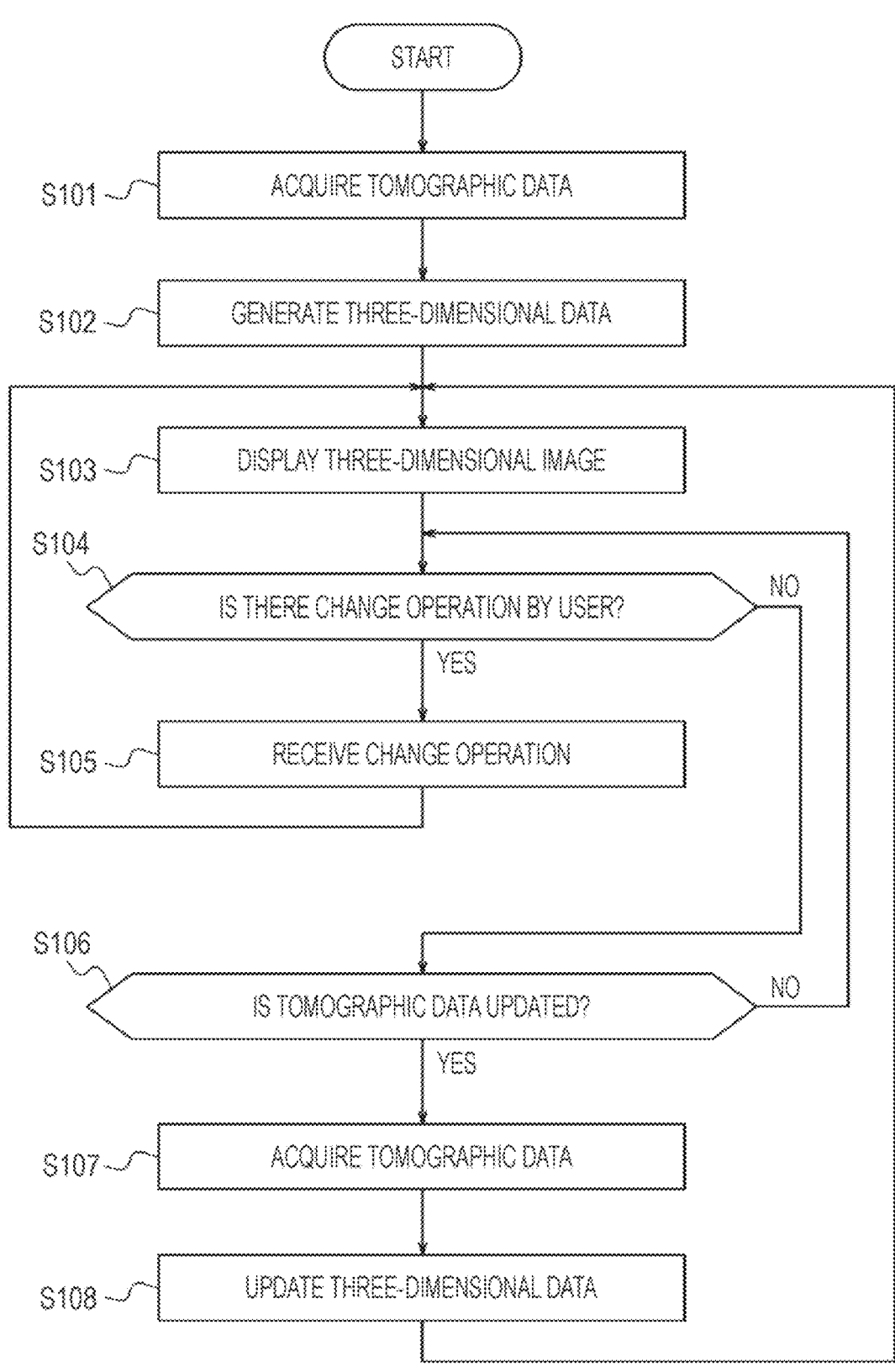
FIG. 7 is a flowchart illustrating operations of the image processing system according to the embodiment of the present disclosure.
Figure 8:
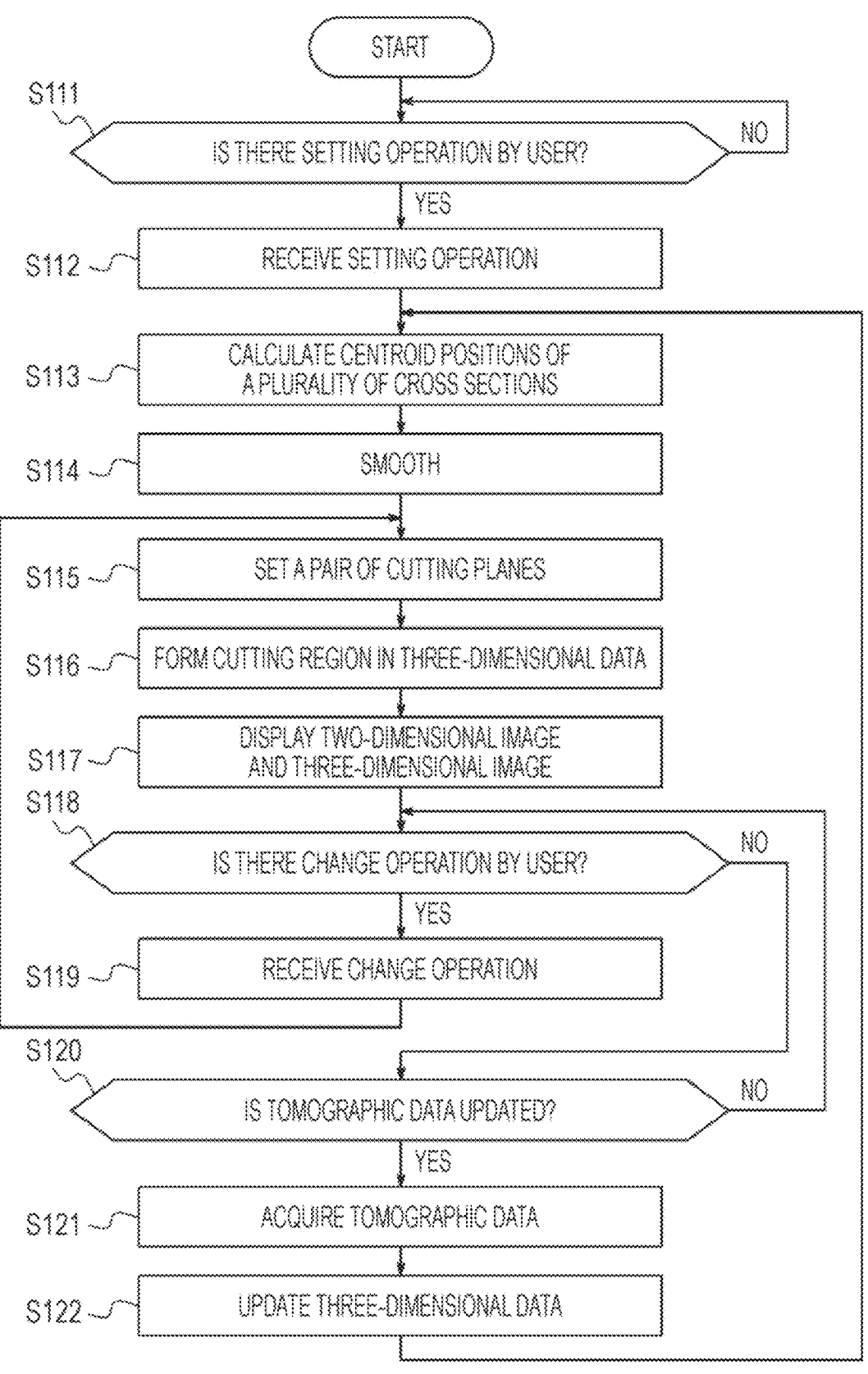
FIG. 8 is a flowchart illustrating operations of the image processing system according to the embodiment of the present disclosure.

Before a start of a flow of FIG. 7, the probe 20 is primed by the user. Thereafter, the probe 20 is fitted into the probe connection portion 34 and the probe clamp portion 37 of the drive unit 13, and is connected and fixed to the drive unit 13. Then, the probe 20 is inserted to a target site in the biological tissue 60 such as a blood vessel or the heart.

In S101, the scan switch included in the switch group 39 is pressed, and the pull-back switch included in the switch group 39 is further pressed, so that a so-called pull-back operation is performed. The probe 20 transmits an ultrasonic wave inside the biological tissue 60 by the ultrasound transducer 25 that moves backward in the axial direction by the pull-back operation. The ultrasound transducer 25 radially transmits the ultrasound wave while moving inside the biological tissue 60. The ultrasound transducer 25 receives a reflected wave of the transmitted ultrasound wave. The probe 20 inputs a signal of the reflected wave received by the ultrasound transducer 25 to the image processing device 11. The control unit 41 of the image processing device 11 processes the input signal to sequentially generate cross-sectional images of the biological tissue 60, thereby acquiring the tomographic data 51, which includes a plurality of cross-sectional images.

Specifically, the probe 20 transmits the ultrasonic wave in a plurality of directions from a rotation center to the outside by the ultrasound transducer 25 while rotating the ultrasound transducer 25 in the circumferential direction and moving the ultrasound transducer 25 in the axial direction inside the biological tissue 60. The probe 20 receives the reflected wave from a reflecting object existing in each of a plurality of directions inside the biological tissue 60 by the ultrasound transducer 25. The probe 20 transmits the signal of the received reflected wave to the image processing device 11 via the drive unit 13 and the cable 12. The communication unit 43 of the image processing device 11 receives the signal transmitted from the probe 20. The communication unit 43 performs A/D conversion on the received signal. The communication unit 43 inputs the A/D converted signal to the control unit 41. The control unit 41 processes the input signal to calculate an intensity value distribution of the reflected wave from the reflecting object existing in the transmission direction of the ultrasonic wave of the ultrasound transducer 25. The control unit 41 sequentially generates two-dimensional images having a luminance value distribution corresponding to the calculated intensity value distribution as the cross-sectional images of the biological tissue 60, thereby acquiring tomographic data 51, which is a data set of the cross-sectional images. The control unit 41 stores the acquired tomographic data 51 in the storage unit 42.

In the present embodiment, the signals of the reflected wave received by the ultrasound transducer 25 corresponds to raw data of the tomographic data 51, and the cross-sectional images generated by processing the signal of the reflected wave by the image processing device 11 correspond to processed data of the tomographic data 51.

In a modification of the present embodiment, the control unit 41 of the image processing device 11 may store the signal input from the probe 20 as it is in the storage unit 42 as the tomographic data 51. Alternatively, the control unit 41 may store data indicating the intensity value distribution of the reflected wave calculated by processing the signal input from the probe 20 in the storage unit 42 as the tomographic data 51. That is, the tomographic data 51 is not limited to the data set of the cross-sectional images of the biological tissue 60, and may be data representing a cross-section of the biological tissue 60 at each moving position of the ultrasound transducer 25 in any format.

In a modification of the present embodiment, an ultrasound transducer that transmits the ultrasound wave in the plurality of directions without rotating may be used instead of the ultrasound transducer 25 that transmits the ultrasound wave in the plurality of directions while rotating in the circumferential direction.

In a modification of the present embodiment, the tomographic data 51 may be acquired using optical frequency domain imaging (OFDI) or optical coherence tomography (OCT) instead of being acquired using IVUS. In a case where OFDI or OCT is used, as a sensor that acquires the tomographic data 51 while moving in the lumen 63 of the biological tissue 60, a sensor that acquires the tomographic data 51 by emitting light in the lumen 63 of the biological tissue 60 is used instead of the ultrasound transducer 25 that acquires the tomographic data 51 by transmitting the ultrasound wave in the lumen 63 of the biological tissue 60.

In a modification of the present embodiment, instead of the image processing device 11 generating the data set of the cross-sectional images of the biological tissue 60, another device may generate a similar data set, and the image processing device 11 may acquire the data set from the other device. That is, instead of the control unit 41 of the image processing device 11 processing the IVUS signal to generate the cross-sectional images of the biological tissue 60, another device may process the IVUS signal to generate the cross-sectional images of the biological tissue 60 and input the generated cross-sectional images to the image processing device 11.

In S102, the control unit 41 of the image processing device 11 generates the three-dimensional data 52 of the biological tissue 60 based on the tomographic data 51 acquired in S101. That is, the control unit 41 generates the three-dimensional data 52 based on the tomographic data 51 acquired by the sensor. Note that at this time, if already generated three-dimensional data 52 is present, it is preferable to update only data at a location corresponding to the updated tomographic data 51, instead of regenerating all the three-dimensional data 52 from the beginning. Accordingly, a data processing amount when generating the three-dimensional data 52 can be reduced, and a real-time property of the three-dimensional image 53 in the subsequent S103 can be improved.

Specifically, the control unit 41 of the image processing device 11 generates the three-dimensional data 52 of the biological tissue 60 by layering the cross-sectional images of the biological tissue 60 included in the tomographic data 51 stored in the storage unit 42 and converting the same into three-dimensional data. As a method of three-dimensional conversion, any method among rendering methods such as surface rendering or volume rendering, and various types of processing associated with the rendering method such as texture mapping including environment mapping and bump mapping can be used. The control unit 41 stores the generated three-dimensional data 52 in the storage unit 42.

In S103, the control unit 41 of the image processing device 11 displays the three-dimensional data 52 generated in S102 on the display 16, as the three-dimensional image 53. The control unit 41 may set an angle for displaying the three-dimensional image 53 to any angle.

Specifically, the control unit 41 of the image processing device 11 generates the three-dimensional image 53 based on the three-dimensional data 52 stored in the storage unit 42. The control unit 41 displays the generated three-dimensional image 53 on the display 16 via the output unit 45.

In S104, if there is an operation of setting the angle for displaying the three-dimensional image 53 as a change operation by the user, processing of S105 is performed. If there is no change operation by the user, processing of S106 is performed.

In S105, the control unit 41 of the image processing device 11 receives, via the input unit 44, the operation of setting the angle for displaying the three-dimensional image 53. The control unit 41 adjusts the angle for displaying the three-dimensional image 53 to the set angle. In S103, the control unit 41 causes the display 16 to display the three-dimensional image 53 at the angle set in S105.

Specifically, the control unit 41 of the image processing device 11 receives, via the input unit 44, an operation by the user of rotating the three-dimensional image 53 displayed on the display 16 by using the keyboard 14, the mouse 15, or the touch screen disposed integrally with the display 16. The control unit 41 interactively adjusts the angle for displaying the three-dimensional image 53 on the display 16 according to the operation by the user. Alternatively, the control unit 41 receives, via the input unit 44, an operation by the user of inputting a numerical value of the angle for displaying the three-dimensional image 53 by using the keyboard 14, the mouse 15, or the touch screen disposed integrally with the display 16. The control unit 41 adjusts the angle for displaying the three-dimensional image 53 on the display 16 in accordance with the input numerical value.

If the tomographic data 51 is updated in S106, the processing in S107 and S108 is performed. If the tomographic data 51 is not updated, the presence or absence of the change operation by the user is confirmed again in S104.

In S107, similarly to the processing in S101, the control unit 41 of the image processing device 11 processes the signal input from the probe 20 to newly generate cross-sectional images of the biological tissue 60, thereby acquiring the tomographic data 51 including at least one new cross-sectional image.

In S108, the control unit 41 of the image processing device 11 updates the three-dimensional data 52 of the biological tissue 60 based on the tomographic data 51 acquired in S107. That is, the control unit 41 updates the three-dimensional data 52 based on the tomographic data 51 acquired by the sensor. Then, in S103, the control unit 41 displays the three-dimensional data 52 updated in S108 on the display 16, as the three-dimensional image 53. In S108, it is preferable to update only data at a location corresponding to the updated tomographic data 51. Accordingly, the data processing amount when generating the three-dimensional data 52 can be reduced, and the real-time property of the three-dimensional image 53 can be improved in S108.

In S111, if there is an operation of setting an angle between the cutting planes P1 and P2 as illustrated in FIG. 4 as a setting operation by the user, the processing of S112 is performed.

In S112, the control unit 41 of the image processing device 11 receives, via the input unit 44, the operation of setting the angle between the cutting planes P1 and P2.

Specifically, the control unit 41 of the image processing device 11 receives, via the input unit 44, an operation by the user of inputting a numerical value of the angle between the cutting planes P1 and P2 using the keyboard 14, the mouse 15, or the touch screen disposed integrally with the display 16.

In S113, the control unit 41 of the image processing device 11 calculates the centroid positions of the plurality of lateral cross sections of the lumen 63 of the biological tissue 60 by using the latest three-dimensional data 52 stored in the storage unit 42. The latest three-dimensional data 52 is the three-dimensional data 52 generated in S102 if the processing in S108 is not performed, and is the three-dimensional data 52 updated in S108 if the processing in S108 is performed. Note that at this time, if already generated three-dimensional data 52 is present, it is preferable to update only data at a location corresponding to the updated tomographic data 51, instead of regenerating all of the three-dimensional data 52 from the beginning. Accordingly, a data processing amount when generating the three-dimensional data 52 can be reduced, and a real-time property of the three-dimensional image 53 in the subsequent S117 can be improved.

Figure 9:
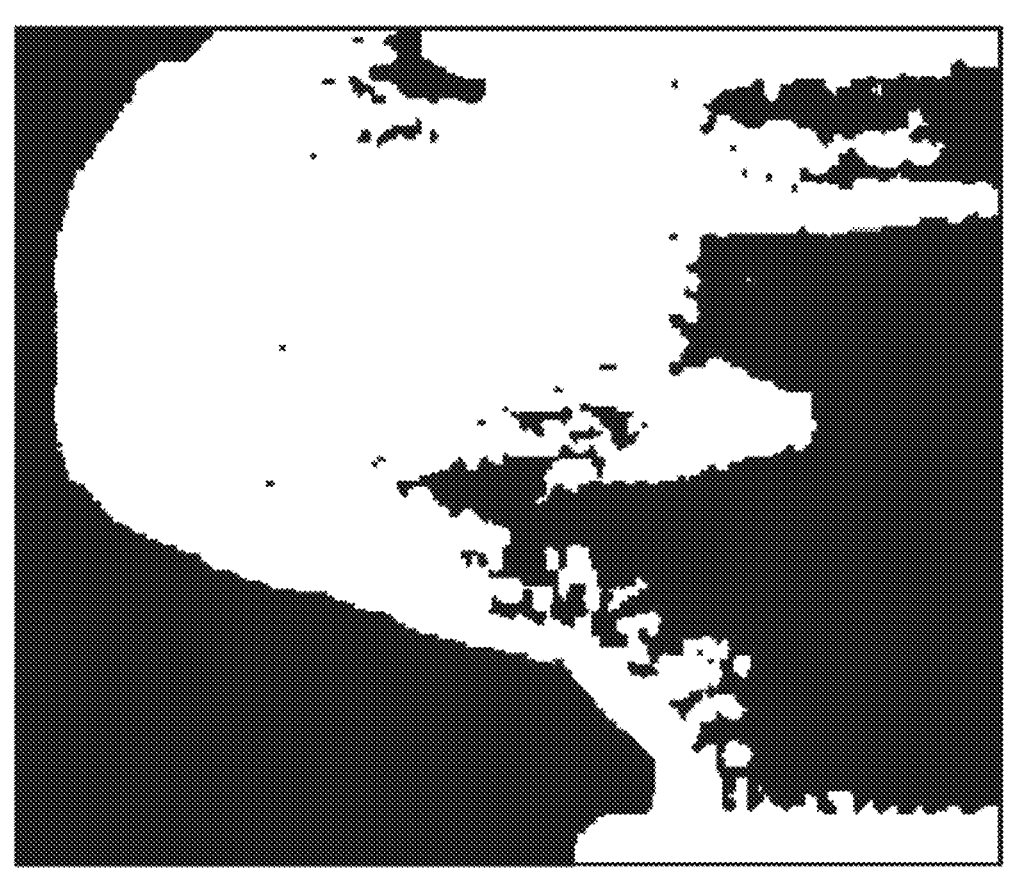
FIG. 9 is a diagram illustrating a result of binarizing a cross-sectional image of a biological tissue in the embodiment of the present disclosure.
Figure 10:
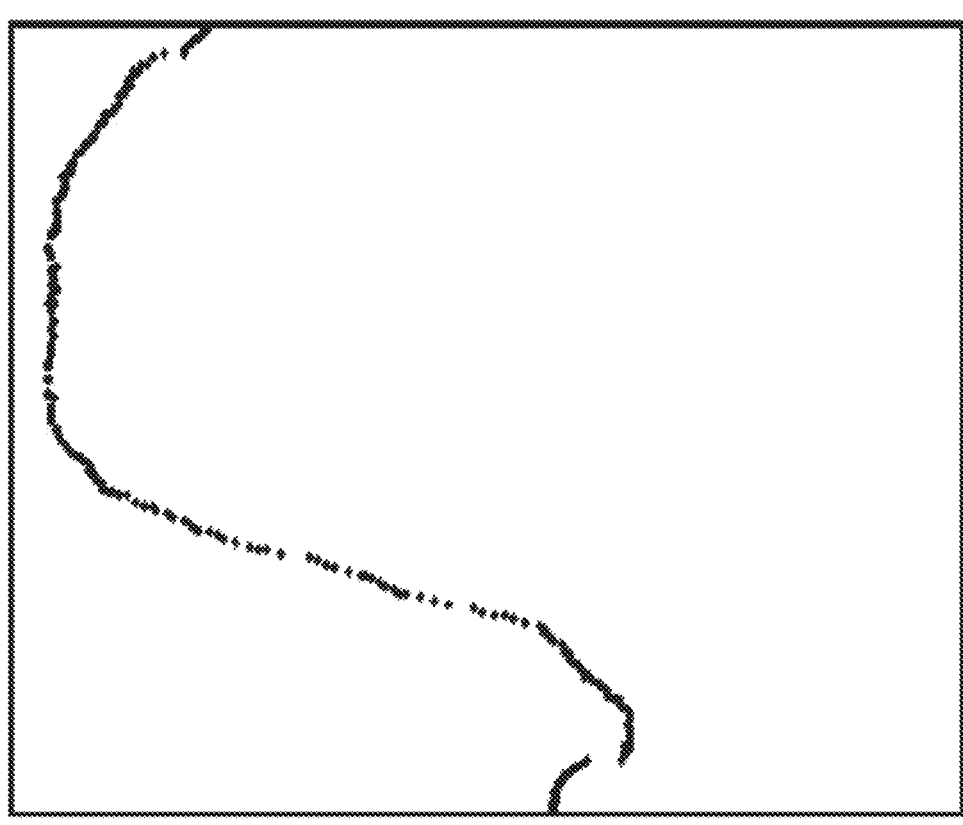
FIG. 10 is a diagram illustrating a result of extracting a point cloud of an inner surface of a biological tissue in the embodiment of the present disclosure.

Specifically, as illustrated in FIG. 9, if the control unit 41 of the image processing device 11 generates a corresponding new cross-sectional image in S107 for each of the plurality of cross-sectional images generated in S101, the control unit 41 replaces each of the plurality of cross-sectional images generated in S101 with the new cross-sectional image, and then binarizes the cross-sectional image. As illustrated in FIG. 10, the control unit 41 extracts a point cloud (i.e., a set of data points) on an inner surface of the biological tissue 60 from the binarized cross-sectional image. For example, the control unit 41 extracts a point cloud on an inner surface of a blood vessel by extracting points corresponding to an inner surface of a main blood vessel one by one along a longitudinal direction of the cross-sectional image with an r-axis as a horizontal axis and a θ-axis as a vertical axis. The control unit 41 may simply obtain the centroid of the extracted point cloud on the inner surface, but in that case, since the point cloud is not uniformly sampled over the inner surface, a centroid position shifts. Therefore, in the present embodiment, the control unit 41 calculates the convex hull of the extracted point cloud on the inner surface, and calculates a centroid position $C_n=(C_x, C_y)$ by using a formula for obtaining the centroid of a polygon as follows. However, in the following formula, it is assumed that n vertices $(x_0, y_0)$, $(x_1, y_1)$, . . . , $(x_{n-1}, y_{n-1})$ are present on the convex hull counterclockwise as the point cloud on the inner surface as illustrated in FIG. 10, and $(x_n, y_n)$ is regarded as $(x_0, y_0)$.

$$C_x = \frac{1}{6A}\sum_{i=0}^{n-1}(x_i + x_{i+1})(x_i y_{i+1} - x_{i+1}y_i)$$ Mathematical formula 1

$$C_y = \frac{1}{6A}\sum_{i=0}^{n-1}(y_i + y_{i+1})(x_i y_{i+1} - x_{i+1}y_i)$$

$$A = \frac{1}{2}\sum_{i=0}^{n-1}(x_i y_{i+1} - x_{i+1}y_i)$$

Figure 11:
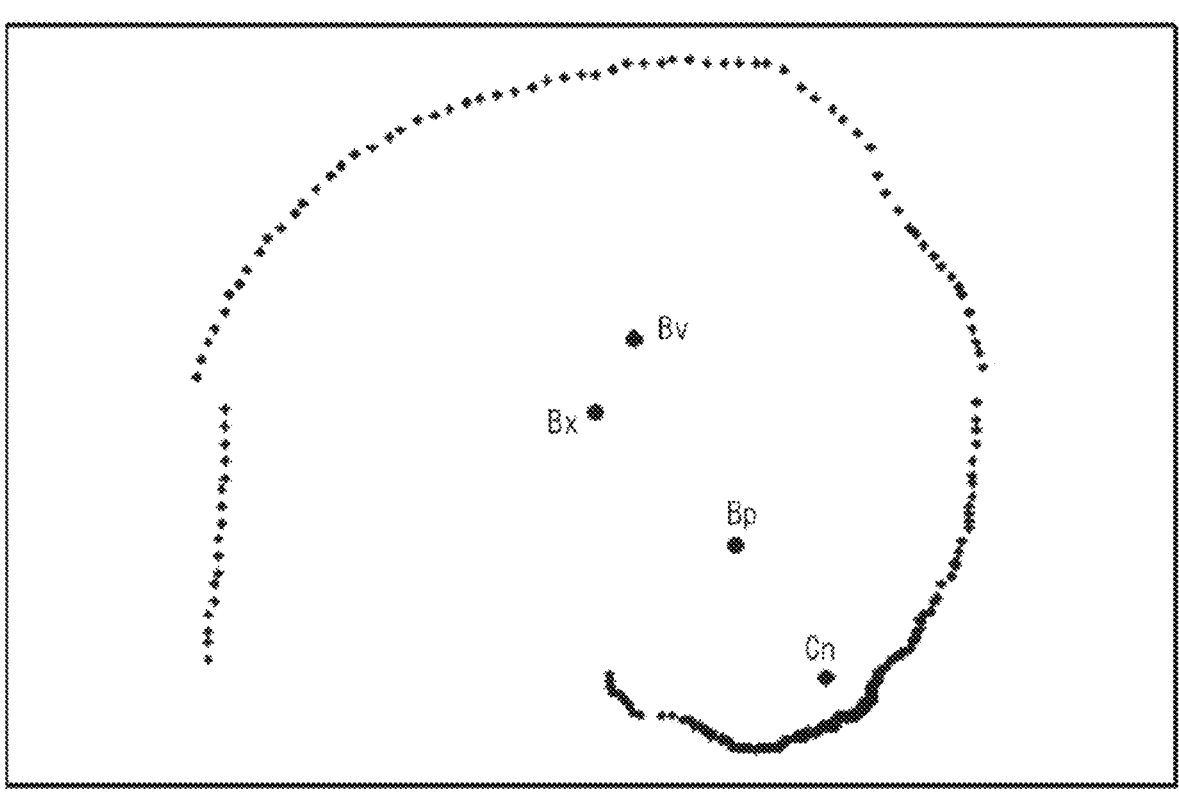
FIG. 11 is a diagram illustrating a result of calculating a centroid position of a cross section of a biological tissue in the embodiment of the present disclosure.

The centroid positions obtained as results are illustrated in FIG. 11. In FIG. 11, a point $C_n$ is the center of the cross-sectional image. A point Bp is a centroid of the point cloud on the inner surface. A point By is a centroid of the vertices of the polygon. A point Bx is a centroid of the polygon serving as a convex hull.

As a method of calculating the centroid position of the blood vessel, a method other than the method of calculating the centroid position of the polygon serving as the convex hull may be used. For example, with respect to an original cross-sectional image that is not binarized, a method of calculating a center position of the maximum circle that falls within the main blood vessel as the centroid position may be used. Alternatively, with respect to the binarized cross-sectional image having the r-axis as the horizontal axis and the θ-axis as the vertical axis, a method of calculating an average position of pixels in a main blood vessel region as the centroid position may be used. The same method as described above may also be used when the biological tissue 60 is not a blood vessel.

In S114, the control unit 41 of the image processing device 11 smooths calculation results of the centroid positions in S113.

Figure 12:
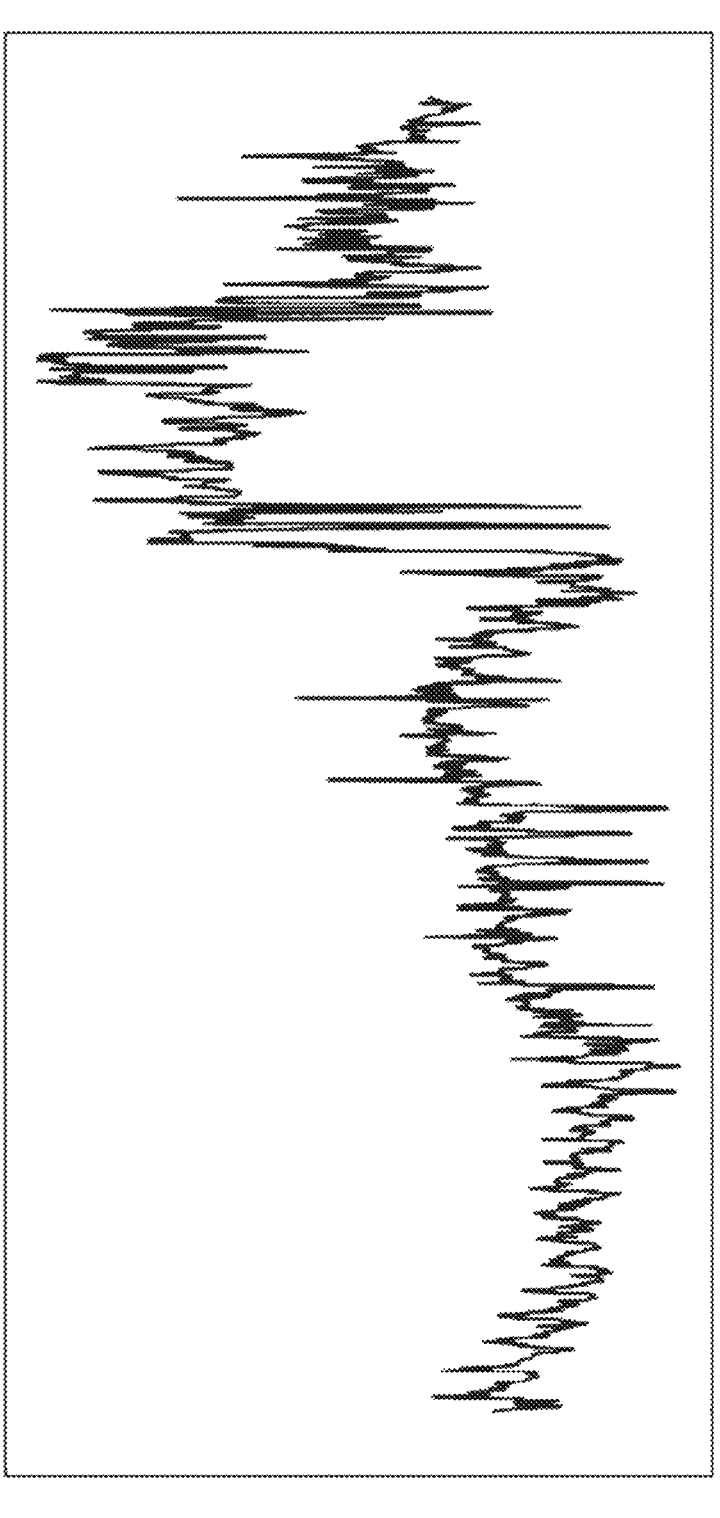
FIG. 12 is a diagram illustrating a result of calculating centroid positions of a plurality of cross sections of a biological tissue in the embodiment of the present disclosure.
Figure 13:
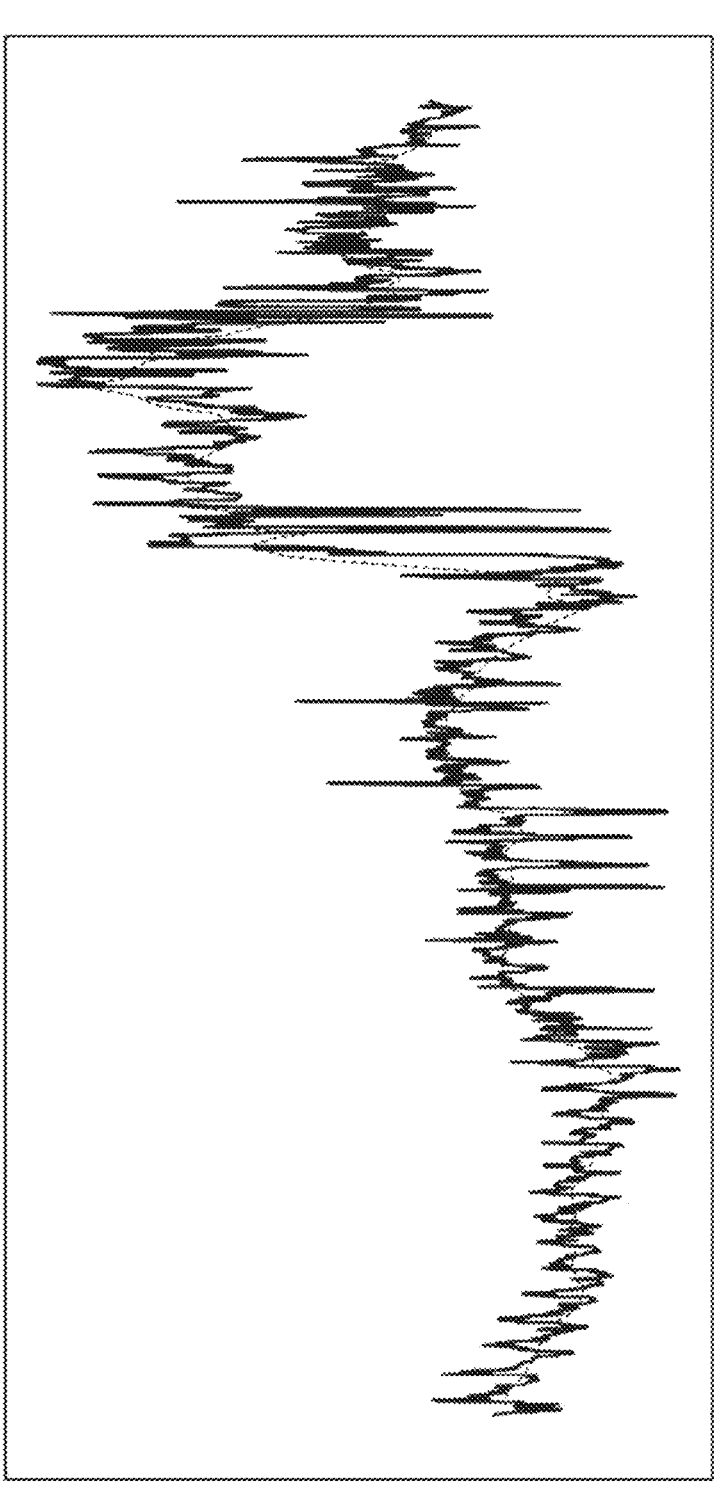
FIG. 13 is a diagram illustrating a result of smoothing the result of FIG. 12.

As illustrated in FIG. 12, when the calculation results of the centroid positions are viewed as a time function, it can be seen that an influence of pulsation is large. Therefore, in the present embodiment, the control unit 41 of the image processing device 11 smooths the calculation results of the centroid positions by using moving averages as indicated by a broken line in FIG. 13.

As a smoothing method, a method other than the moving average may be used. For example, exponential smoothing method, kernel method, local regression, Ramer-Douglas-Peucker algorithm, Savitzky-Golay method, smoothed spline, or stretched grid method (SGM) may be used. Alternatively, a method of executing the fast Fourier transform and then removing a high-frequency component may be used. Alternatively, Kalman filter or a low-pass filter such as Butterworth filter, Chebyshev filter, digital filter, elliptical filter, or Kolmogorov-Zurbenko (KZ) filter may be used.

Simple smoothing may cause the centroid positions to enter the tissue. In this case, the control unit 41 may divide the calculation results of the centroid position, in the longitudinal direction of the lumen 63 of the biological tissue 60, according to positions of the plurality of lateral cross sections of the lumen 63 of the biological tissue 60, and may smooth each of the divided calculation results. That is, when a curve of the centroid positions as indicated by the broken line in FIG. 13 overlaps a tissue region, the control unit 41 may divide the curve of the centroid positions into a plurality of sections and execute individual smoothing for each section. Alternatively, the control unit 41 may adjust a degree of smoothing to be executed on the calculation results of the centroid positions according to the positions of the plurality of lateral cross sections of the lumen 63 of the biological tissue 60 in the longitudinal direction of the lumen 63 of the biological tissue 60. That is, when the curve of the centroid positions as indicated by the broken line in FIG. 13 overlaps the tissue region, the control unit 41 may decrease the degree of smoothing to be executed for a part of the sections including the overlapping points.

In S115, as illustrated in FIG. 4, the control unit 41 of the image processing device 11 sets two planes intersecting at the single line Lb passing through the centroid positions calculated in S113, as cutting planes P1 and P2. In the present embodiment, the control unit 41 smooths the calculation results of the centroid positions in S114, and then sets the cutting planes P1 and P2, but the processing of S114 may be omitted.

Specifically, the control unit 41 of the image processing device 11 sets a curve of the centroid positions obtained as a result of the smoothing in S114 as the line Lb. The control unit 41 sets two planes intersecting at the set line Lb and forming the angle set in S112 as the cutting planes P1 and P2. The control unit 41 specifies three-dimensional coordinates intersecting with the cutting planes P1 and P2 of the biological tissue 60 in the latest three-dimensional data 52 stored in the storage unit 42 as the three-dimensional coordinates of an edge of the opening exposing the lumen 63 of the biological tissue 60 in the three-dimensional image 53. The control unit 41 stores the specified three-dimensional coordinates in the storage unit 42. Positions of the cutting planes P1 and P2 may be set freely, but in the present embodiment, the positions are set such that the opening is positioned in front of the screen of the display 16.

In S116, the control unit 41 of the image processing device 11 forms, in the three-dimensional data 52, a region that is interposed between the cutting planes P1 and P2 in the three-dimensional image 53 and that exposes the lumen 63 of the biological tissue 60, as a cutting region 62.

Specifically, the control unit 41 of the image processing device 11 sets a portion specified by the three-dimensional coordinates stored in the storage unit 42 in the latest three-dimensional data 52 stored in the storage unit 42 to be hidden or transparent when the three-dimensional image 53 is displayed on the display 16.

In S117, the control unit 41 of the image processing device 11 displays the three-dimensional data 52 in which the cutting region 62 is formed in S116 on the display 16, as the three-dimensional image 53. The control unit 41 performs control of displaying a two-dimensional image 54 representing a portion corresponding to the cutting region 62 in one cross section Ci of the biological tissue 60 at a position 65 corresponding to the one cross section Ci in the three-dimensional image 53.

Specifically, the control unit 41 of the image processing device 11 generates the two-dimensional image 54 as illustrated in FIG. 2 by cutting out the latest cross-sectional image among the cross-sectional images of the biological tissue 60 included in the tomographic data 51 stored in the storage unit 42. The control unit 41 generates the three-dimensional image 53 as illustrated in FIG. 2 in which a portion specified by the three-dimensional coordinates stored in the storage unit 42 is hidden or transparent. The control unit 41 displays the two-dimensional image 54 and the three-dimensional image 53 that are generated, on the display 16 via the output unit 45.

In the present embodiment, as illustrated in FIG. 3, in a case where the camera 71 is not on the plane 66 corresponding to the cross section Ci in the three-dimensional image 53, the control unit 41 of the image processing device 11 performs control of displaying the two-dimensional image 54 on the plane 66. In a case where the camera 71 is on the plane 66 in the three-dimensional image 53, a line of sight 72 from the camera 71 to the two-dimensional image 54 is positioned on the plane 66. Therefore, even when it is attempted to display the two-dimensional image 54 on the plane 66, the two-dimensional image 54 becomes invisible. That is, in a case where the camera 71 is on the plane 66 in the three-dimensional image 53, the two-dimensional image 54 cannot be displayed on the plane 66. Therefore, it is conceivable to take the following measures.

Figure 14:
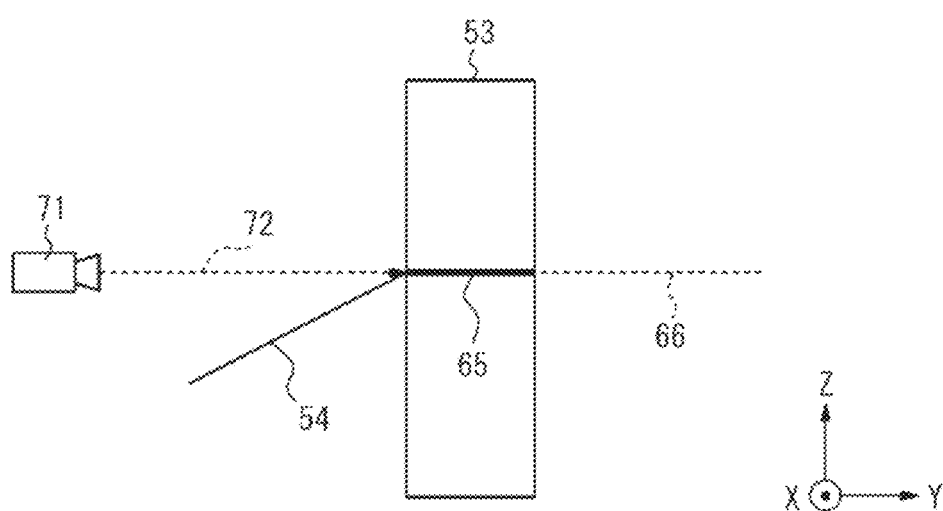
FIG. 14 is a diagram illustrating an example of a positional relationship between an image set by an image processing system according to a first modification of the embodiment of the present disclosure and a camera.

In a first modification of the present embodiment, the two-dimensional image 54 may be displayed in inclination. That is, the two-dimensional image 54 may be displayed at a constant angle with respect to the camera 71. Specifically, as illustrated in FIG. 14, in a case where the camera 71 is on the plane 66, the control unit 41 of the image processing device 11 may perform control of displaying the two-dimensional image 54 in inclination with respect to the plane 66. In the first modification, as illustrated in FIG. 3, in a case where the camera 71 is not on the plane 66, the control unit 41 performs control of displaying the two-dimensional image 54 on the plane 66.

Figure 15:
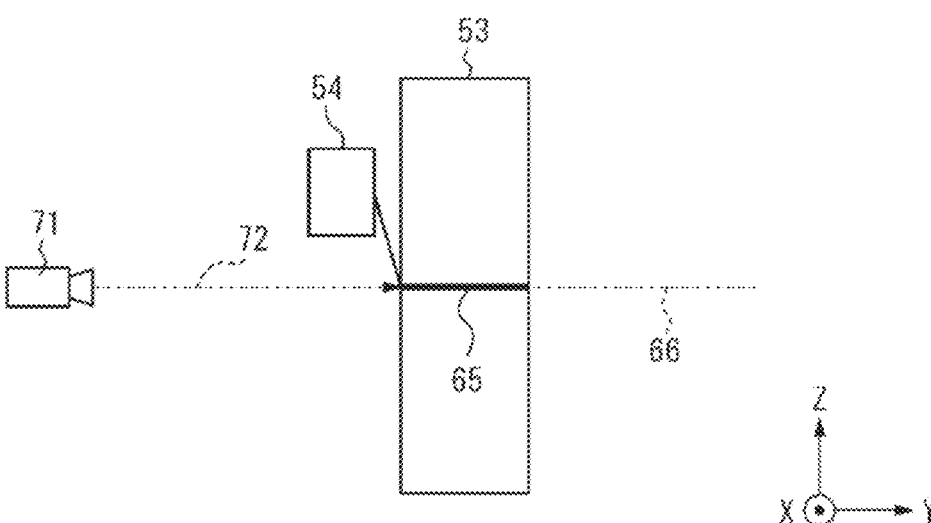
FIG. 15 is a diagram illustrating an example of a positional relationship between an image set by an image processing system according to a second modification of the embodiment of the present disclosure and a camera.
Figure 16A:
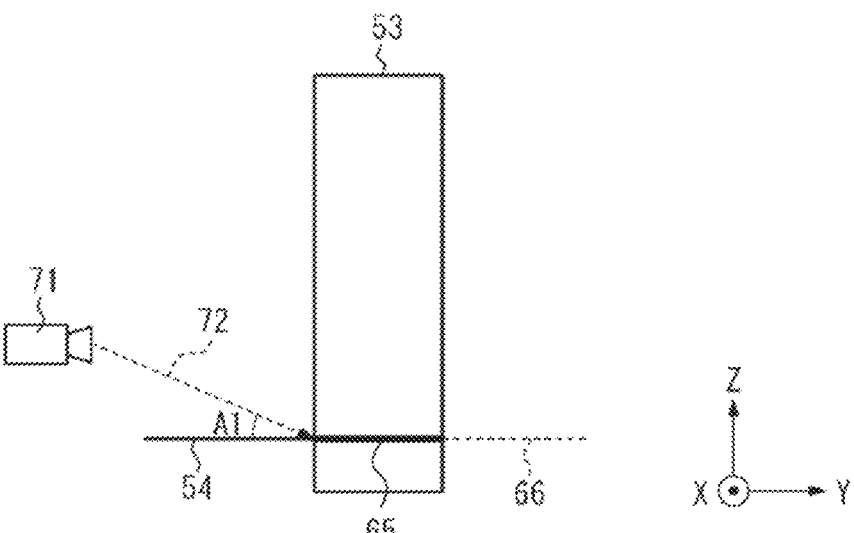
FIG. 16A is a diagram illustrating an example of a positional relationship between an image set by an image processing system according to a third modification of the embodiment of the present disclosure and a camera.
Figure 16B:
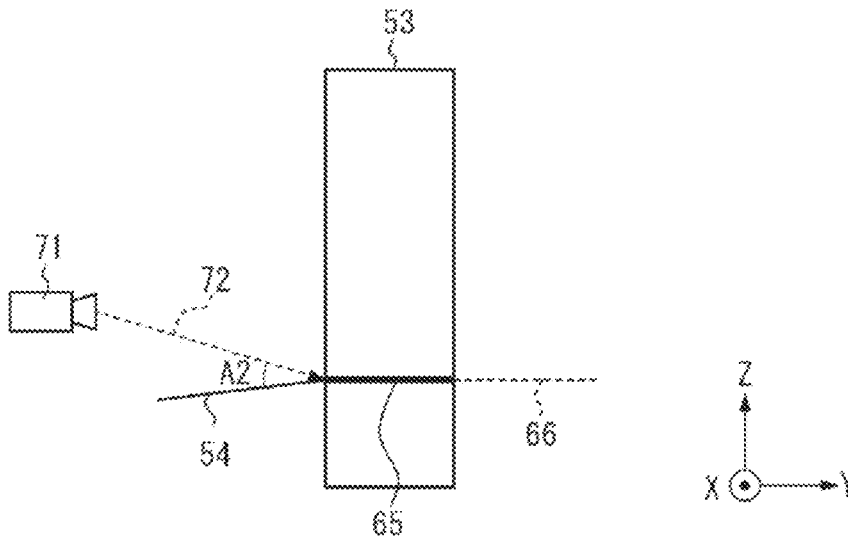
FIG. 16B is a diagram illustrating an example of a positional relationship between an image set by the image processing system according to a third modification of the embodiment of the present disclosure and a camera.
Figure 16C:
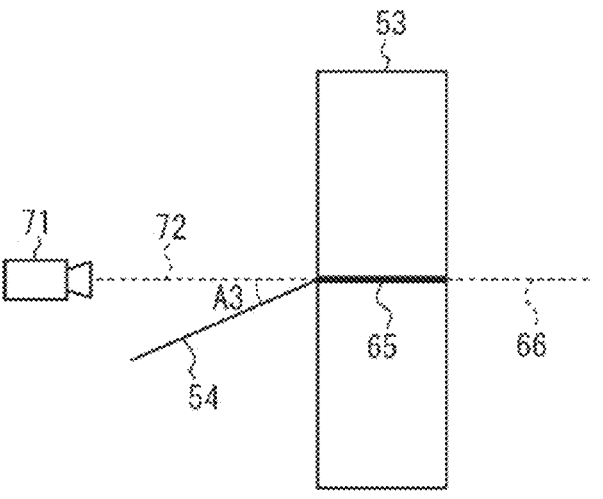
FIG. 16C is a diagram illustrating an example of a positional relationship between an image set by the image processing system according to a third modification of the embodiment of the present disclosure and a camera.
Figure 16C:
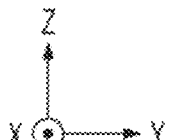
Figure 16D:
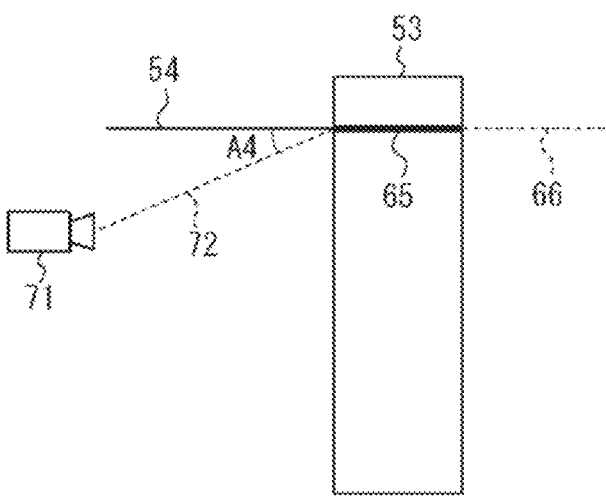
FIG. 16D is a diagram illustrating an example of a positional relationship between an image set by the image processing system according to a third modification of the embodiment of the present disclosure and a camera.
Figure 16D:
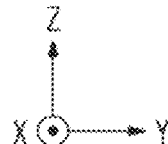

In a second modification of the present embodiment, another window may be temporarily displayed to display the two-dimensional image 54. That is, the two-dimensional image 54 may be displayed in a mini-view. Specifically, as illustrated in FIG. 15, in a case where the camera 71 is on the plane 66, the control unit 41 of the image processing device 11 may perform control of displaying the two-dimensional image 54 on a window other than a window on which the three-dimensional image 53 is displayed. Also in the second modification, as illustrated in FIG. 3, in a case where the camera 71 is not on the plane 66, the control unit 41 performs control of displaying the two-dimensional image 54 on the plane 66.

In a third modification of the present embodiment, the two-dimensional image 54 may be always displayed at the same angle with respect to the camera 71. That is, the two-dimensional image 54 may be maintained at the same angle with respect to the camera 71 so as to be rather easily seen. Specifically, as illustrated in FIGS. 16A to 16D, regardless of whether the camera 71 is on the plane 66 corresponding to the cross section Ci in the three-dimensional image 53, the control unit 41 of the image processing device 11 may adjust the angle at which the two-dimensional image 54 is displayed with respect to the plane 66 to maintain the angle formed between the line of sight 72 from the camera 71 to the two-dimensional image 54 and the two-dimensional image 54 at a fixed angle. The "fixed angle" may be any angle as long as the absolute value is larger than 0 degrees and smaller than 90 degrees. For example, when the sensor moves along the Z direction, the position 65 where the two-dimensional image 54 is displayed also changes along the Z direction, but in the third modification, the angle formed between the line of sight 72 and the two-dimensional image 54 is always constant. That is, in FIGS. 16A, 16B, 16C, and 16D, angles A1, A2, A3, and A4 formed between the line of sight 72 and the two-dimensional image 54 are all the same.

Figure 17A:
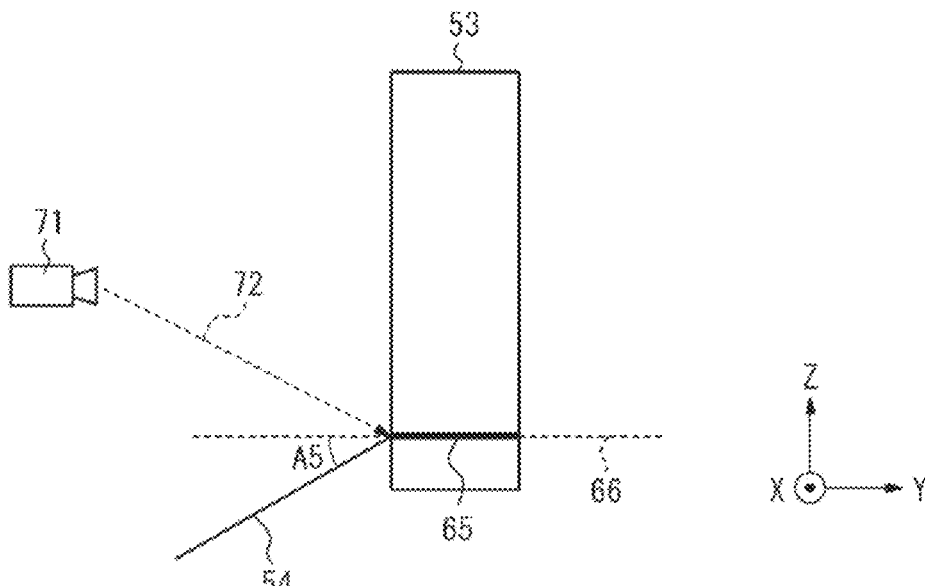
FIG. 17A is a diagram illustrating an example of a positional relationship between an image set by an image processing system according to a fourth modification of the embodiment of the present disclosure and a camera.
Figure 17B:
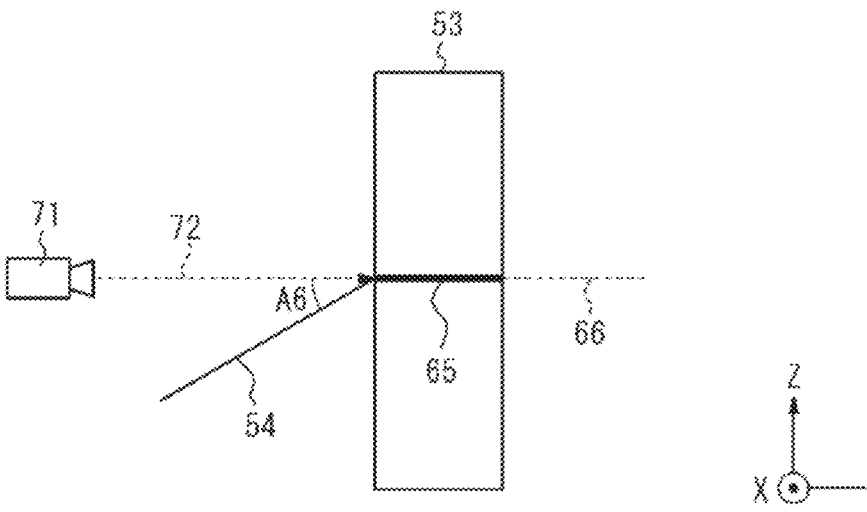
FIG. 17B is a diagram illustrating an example of a positional relationship between an image set by the image processing system according to a fourth modification of the embodiment of the present disclosure and a camera.
Figure 17C:
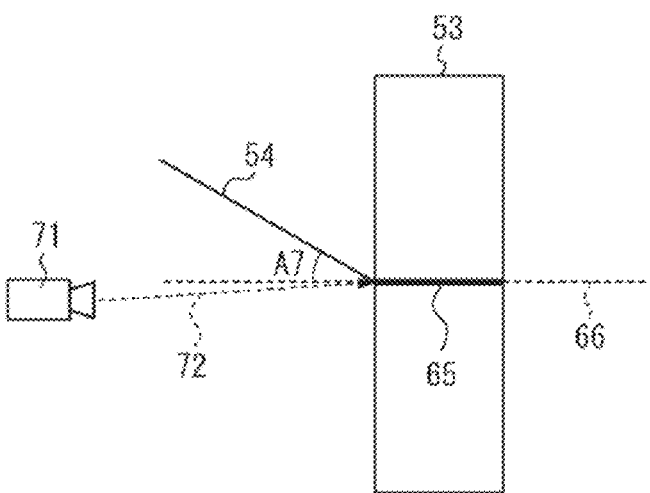
FIG. 17C is a diagram illustrating an example of a positional relationship between an image set by the image processing system according to a fourth modification of the embodiment of the present disclosure and a camera.
Figure 17C:
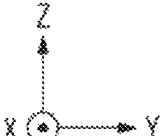
Figure 17D:
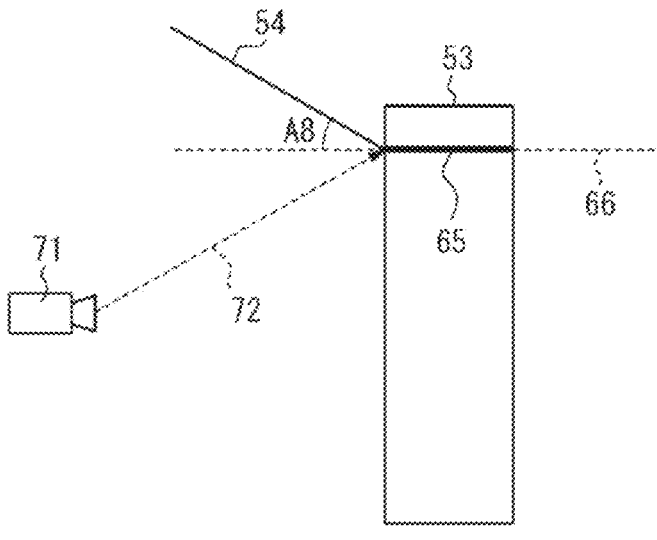
FIG. 17D is a diagram illustrating an example of a positional relationship between an image set by the image processing system according to a fourth modification of the embodiment of the present disclosure and a camera.
Figure 17D:
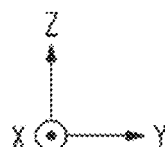

In a fourth modification of the present embodiment, the two-dimensional image 54 may be displayed always in inclination. Specifically, as illustrated in FIGS. 17A to 17D, regardless of whether the camera 71 is on the plane 66 corresponding to the cross section Ci in the three-dimensional image 53, the control unit 41 of the image processing device 11 may adjust the angle at which the two-dimensional image 54 is displayed with respect to the plane 66 to maintain the absolute value of the angle at a fixed value. The "fixed value" may be any angle as long as it is larger than 0 degrees and smaller than 90 degrees. In the fourth modification, as illustrated in FIG. 17A, in a case where the camera 71 is above the plane 66, the control unit 41 performs control of displaying the two-dimensional image 54 in inclination obliquely downward with respect to the plane 66. In this modification, as illustrated in FIG. 17B, even in a case where the camera 71 is on the plane 66, the control unit 41 performs control of displaying the two-dimensional image 54 in inclination obliquely downward with respect to the plane 66. However, in a case where the camera 71 is on the plane 66, the control unit may perform control of displaying the two-dimensional image 54 in inclination obliquely upward with respect to the plane 66. As illustrated in FIGS. 17C and 17D, in a case where the camera 71 is below the plane 66, the control unit 41 performs control of displaying the two-dimensional image 54 in inclination obliquely upward with respect to the plane 66. Therefore, it is relatively easy to avoid a situation in which the two-dimensional image 54 overlaps most of the three-dimensional image 53 and most of the three-dimensional image 53 is invisible. For example, when the sensor moves along the Z direction, the position 65 where the two-dimensional image 54 is displayed also changes along the Z direction, but in the fourth modification, the absolute value of the angle formed between the plane 66 and the two-dimensional image 54 is always constant. That is, in FIGS. 17A, 17B, 17C, and 17D, the absolute values of the angles A5, A6, A7, and A8 formed between the plane 66 and the two-dimensional image 54 are all the same.

In S118, if there is an operation of setting the angle between the cutting planes P1 and P2 or an operation of setting the angle at which the three-dimensional image 53 is displayed as a change operation by the user, processing of S119 is performed. If there is no change operation by the user, processing of S120 is performed.

In S119, the control unit 41 of the image processing device 11 receives, via the input unit 44, the operation of setting the angle between the cutting planes P1 and P2, similarly to the processing in S112. In that case, the processing in S115 and the subsequent steps is performed. Alternatively, the control unit 41 receives, via the input unit 44, the operation of setting the angle for displaying the three-dimensional image 53, similarly to the processing in S105. The control unit 41 adjusts the angle for displaying the three-dimensional image 53 to the set angle. Also in this case, the processing in S115 and the subsequent steps is performed. In S115, the control unit 41 adjusts the positions of the cutting planes P1 and P2 according to the set angle at which the three-dimensional image 53 is displayed. That is, the positions of the cutting planes P1 and P2 are adjusted again such that the opening is positioned in front on the screen of the display 16.

If the tomographic data 51 is updated in S120, the processing in S121 and S122 is performed. If the tomographic data 51 is not updated, the presence or absence of the change operation by the user is confirmed again in S118.

In S121, similarly to the processing in S101 or S107, the control unit 41 of the image processing device 11 processes the signal input from the probe 20 to newly generate cross-sectional images of the biological tissue 60, thereby acquiring the tomographic data 51 including at least one new cross-sectional image.

In S122, the control unit 41 of the image processing device 11 updates the three-dimensional data 52 of the biological tissue 60 based on the tomographic data 51 acquired in S121. Thereafter, the processing in S113 and the subsequent steps is performed. In S122, it is preferable to update only data at a location corresponding to the updated tomographic data 51. Accordingly, the data processing amount when generating the three-dimensional data 52 can be reduced, and the real-time property of data processing in S113 and subsequent steps or processes.

As described above, in the present embodiment, the control unit 41 of the image processing device 11 causes a display 16 to display, as a three-dimensional image 53, three-dimensional data 52 representing a biological tissue 60. The control unit 41 forms, in the three-dimensional data 52, a cutting region 62 for exposing a lumen 63 of the biological tissue 60 in the three-dimensional image 53. The control unit 41 performs control of displaying a two-dimensional image 54 representing a portion corresponding to the cutting region 62 in one cross section Ci of the biological tissue 60 at a position 65 corresponding to the one cross section Ci in the three-dimensional image 53.

According to the present embodiment, it is possible to supplement information about the cut-out portion of the structure of the biological tissue 60.

The present disclosure is not limited to the above-described embodiment. For example, two or more blocks described in the block diagrams may be integrated, or one block may be divided. Instead of executing a plurality of steps or processes described in the flowchart in time series according to the description, the steps or processes may be executed in parallel or in a different order according to the processing capability of the device that executes each step or process, or as necessary. In addition, modifications can be made without departing from the gist of the present disclosure.

The detailed description above describes embodiments of an image processing device, an image processing system, an image display method, and an image processing program. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. An image processing device configured to cause a display to display, as a three-dimensional image, three-dimensional data representing a biological tissue, the image processing device comprising:

a control unit configured to:

acquire tomographic data as the three-dimensional data, the tomographic data including a plurality of cross-sectional images of the biological tissue;

generate the three-dimensional image based on the plurality of cross- sectional images;

form, in the three-dimensional data, a cutting region for exposing a lumen of the biological tissue in the three-dimensional image;

generate a two-dimensional image representing a portion corresponding to the cutting region in one of the plurality of cross-sectional images;

display, on the display, the two-dimensional image at a position corresponding to a cross-sectional position of the one of the plurality of cross-sectional images in the three-dimensional image; and set a viewpoint when the three-dimensional image is displayed by positioning a virtual camera in a three-dimensional space, wherein in a case where the virtual camera is not on a plane corresponding to the cross-sectional position in the three-dimensional image, the control unit is configured to display, on the display, the two-dimensional image on the plane, and wherein in a case where the virtual camera is on the plane, the control unit is configured to display, on the display, the two-dimensional image in inclination with respect to the plane.

2. The image processing device according to claim 1, wherein the control unit is configured to:

generate and update the three-dimensional data based on the plurality of cross-sectional images of the biological tissue acquired by a sensor that acquires tomographic data of the biological tissue while moving in a lumen of the biological tissue;

generate, as the two-dimensional image, an image representing a portion corresponding to the cutting region in a cross-sectional image of the biological tissue newly acquired by the sensor; and display, on the display, the two-dimensional image at a position corresponding to a cross-sectional position of the newly acquired cross-sectional image in the three-dimensional image every time new tomographic data is acquired by the sensor.

3. The image processing device according to claim 1, wherein the control unit is configured to display, on the display, the two-dimensional image on a window other than a window on which the three-dimensional image is displayed in a case where the virtual camera is on the plane.

4. An image processing system comprising:

the image processing device according to claim 1; and a probe including a sensor configured to acquire tomographic data of the biological tissue while moving in a lumen of the biological tissue.

5. The image processing system according to claim 4, further comprising:

the display.

6. An image display method for causing a display to display, as a three-dimensional image, three-dimensional data representing a biological tissue, the image display method comprising:

acquiring, by a computer, tomographic data as the three-dimensional data, the tomographic data including a plurality of cross-sectional images of the biological tissue;

generating, by the computer, the three-dimensional image based on the plurality of cross-sectional images;

forming, by the computer, in the three-dimensional data, a cutting region for exposing a lumen of the biological tissue in the three-dimensional image;

generating, by the computer, a two-dimensional image representing a portion corresponding to the cutting region in one of the plurality of cross-sectional images;

displaying, by the computer, the two-dimensional image at a position corresponding to a cross-sectional position of the one of the plurality of cross-sectional images in the three-dimensional image;

setting, by the computer, a viewpoint when the three-dimensional image is displayed by positioning a virtual camera in a three-dimensional space;

wherein in a case where the virtual camera is not on a plane corresponding to the cross-sectional position in the three-dimensional image, the displaying, on the display, the two-dimensional image on the plane; and wherein in a case where the virtual camera is on the plane, the displaying, on the display, the two-dimensional image in inclination with respect to the plane.

7. The image display method according to claim 6, further comprising:

generating and updating, by the computer, the three-dimensional data based on the plurality of cross-sectional images of the biological tissue acquired by a sensor that acquires tomographic data of the biological tissue while moving in a lumen of the biological tissue; and displaying, on the display, the two-dimensional image at a position corresponding to a cross-sectional position of the newly acquired cross-sectional image in the three-dimensional image every time new is acquired by the sensor.

8. An image processing device configured to cause a display to display, as a three-dimensional image, three-dimensional data representing a biological tissue, the image processing device comprising:

a control unit configured to:

acquire tomographic data as the three-dimensional data, the tomographic data including a plurality of cross-sectional images of the biological tissue;

generate the three-dimensional image based on the plurality of cross- sectional images;

form, in the three-dimensional data, a cutting region for exposing a lumen of the biological tissue in the three-dimensional image;

generate a two-dimensional image representing a portion corresponding to the cutting region in one of the plurality of cross-sectional images;

display, on the display, the two-dimensional image at a position corresponding to a cross-sectional position of the one of the plurality of cross-sectional images in the three-dimensional image;

set a viewpoint when the three-dimensional image is displayed by positioning a virtual camera in a three-dimensional space;

wherein the control unit is configured to display, on the display, the two-dimensional image in inclination obliquely downward with respect to the plane in a case where the virtual camera is above a plane corresponding to the cross-sectional position in the three-dimensional image; and wherein the control unit is configured to display, on the display, the two-dimensional image in inclination obliquely upward with respect to the plane in a case where the virtual camera is below the plane.

9. An image display method for causing a display to display, as a three-dimensional image, three-dimensional data representing a biological tissue, the image display method comprising:

acquiring, by a computer, tomographic data as the three-dimensional data, the tomographic data including a plurality of cross-sectional images of the biological tissue;

generating, by the computer, the three-dimensional image based on the plurality of cross-sectional images;

forming, by the computer, in the three-dimensional data, a cutting region for exposing a lumen of the biological tissue in the three-dimensional image;

generating, by the computer, a two-dimensional image representing a portion corresponding to the cutting region in one of the plurality of cross-sectional images;

displaying, on the display, the two-dimensional image at a position corresponding to a cross-sectional position of the one of the plurality of cross-sectional images in the three-dimensional image;

setting, by the computer, a viewpoint when the three-dimensional image is displayed by positioning a virtual camera in a three-dimensional space;

wherein the computer is configured to display, on the display, the two-dimensional image in inclination obliquely downward with respect to the plane in a case where the virtual camera is above a plane corresponding to the cross-sectional position in the three-dimensional image; and wherein the computer is configured to display, on the display, the two-dimensional image in inclination obliquely upward with respect to the plane in a case where the virtual camera is below the plane.

* * * * *